(12) United States Patent
Dargis et al.

(10) Patent No.: US 10,856,825 B2
(45) Date of Patent: Dec. 8, 2020

(54) RADIOGRAPHIC IMAGING APPARATUS

(71) Applicant: Shimadzu Corporation, Kyoto (JP)

(72) Inventors: Michel Dargis, Laval (CA); Wataru Takahashi, Kyoto (JP); Keiichi Goto, Kyoto (JP)

(73) Assignee: Shimadzu Corporation, Kyoto (JP)

(*) Notice: Subject to any disclaimer, the term of this patent is extended or adjusted under 35 U.S.C. 154(b) by 326 days.

(21) Appl. No.: 15/922,977

(22) Filed: Mar. 16, 2018

(65) Prior Publication Data
US 2019/0282190 A1 Sep. 19, 2019

(51) Int. Cl.
*A61B 6/00* (2006.01)
*G06T 7/11* (2017.01)

(52) U.S. Cl.
CPC ............... *A61B 6/469* (2013.01); *A61B 6/42* (2013.01); *A61B 6/54* (2013.01); *G06T 7/11* (2017.01); *G06T 2207/10124* (2013.01)

(58) Field of Classification Search
None
See application file for complete search history.

(56) References Cited

U.S. PATENT DOCUMENTS

2007/0238963 A1* 10/2007 Kaminaga ............ A61B 6/488
600/407

2012/0134566 A1* 5/2012 Nitta ..................... A61B 6/5223
382/131
2013/0257865 A1 10/2013 Kobayashi

FOREIGN PATENT DOCUMENTS

JP 2005-287524 A 10/2005
JP 2013-027697 A 2/2013

* cited by examiner

*Primary Examiner* — Matthew C Bella
*Assistant Examiner* — Brian D Shin
(74) *Attorney, Agent, or Firm* — Muir Patent Law, PLLC

(57) ABSTRACT

[Purpose] To provide a radiographic imaging apparatus capable of quickly acquiring three-dimensional image data of a target-of-interest when performing an operative procedure such as interventional treatment
[Solving Means] A region-of-interest extraction unit 39 extracts a predetermined region as a region-of-interest from each of a series of two-dimensional images. The reconstruction unit 41 reconstructs a three-dimensional image of a region including a stent based on each of the images of the portion corresponding to the region-of-interest. That is, since the reconstruction unit 41 reconstructs each of a series of two-dimensional images P using an image of the region-of-interest corresponding to a part of the whole, the time required to reconstruct the three-dimensional image of the region including the stent can be shortened. As a result, since three-dimensional image data can be quickly obtained for the region requiring the reconstruction, the time required for diagnosis can be greatly shortened, which can reduce the burden on a surgeon and a subject.

17 Claims, 16 Drawing Sheets

RADIOGRAPHIC IMAGING APPARATUS

TECHNICAL FIELD

The present invention relates to a radiographic imaging apparatus which can be effectively used for, e.g., an interventional treatment and is configured to capture an image of a region including a device inserted in a body of a subject, and more particularly to a technology for generating and displaying a three-dimensional image of the device.

BACKGROUND ART

At a medical site, an interventional treatment (IVR: Interventional Radiography) is performed on a patient with blood vessels stenosed by an atheroma or calcified blood vessel wall. In an interventional procedure, a catheter equipped with a guide wire therein is inserted into a blood vessel of a subject to carry out a treatment of an affected part of the stenosed blood vessel.

As an endovascular treatment by a catheter, besides cutting of a blood vessel wall using a roller bladder, stent indwelling using a stent can be exemplified. A stent is a lattice-shaped cylindrical member constituted by a metal wire such as a stainless steel wire, and is equipped with a balloon (not shown) therein. In an IVR, a stent is placed at a narrowed part of a blood vessel. Then, the placed stent is expanded with a balloon. By placing the expanded stent in the blood vessel to expand the stenosed portion of the blood vessel, the blood flow can be kept normal.

In the case of performing an IVR operative procedure using a stent, imaging of a radiation image is performed using a radiographic imaging apparatus in order to confirm the position of the stent. That is, a surgeon irradiates a low dose of radiation to a subject to continuously acquire radiation images in which a catheter and a stent appear are reflected. A surgeon refers to the continuously displayed real-time radiation images to check the positions of the catheter and the stent in the blood vessel as needed, so that the stent can be placed at the appropriate position of the stenosed segment.

In recent years, there is a growing need to acquire a three-dimensional image reflecting the region including the stent during an IVR treatment for the purpose of improving the therapeutic effect. As an example of a conventional radiographic imaging apparatus capable of acquiring a three-dimensional image of a stent, a configuration as disclosed in Patent Document 1 can be exemplified. As shown in FIG. 17 (a), the radiographic imaging apparatus 101 according to the conventional example is equipped with a top board 103 on which a subject M taking a horizontal posture is placed, a radiation source 105, and a radiation detector 107. As an example of the radiation detector 107, a flat panel type detector (FPD) or the like is used.

The radiation source 105 and the radiation detector 107 are opposed to each other across the top board 103, and are provided at one end of the C-shaped arm 109 and the other end thereof, respectively. The C-shaped arm 109 is configured to slide along the circular arc path of the C-shaped arm 109 indicated by the reference symbol "RA". Furthermore, the C-shaped arm 109 is configured to be rotatable about the axis of the horizontal axis RB parallel to the x-direction (the longitudinal direction of the top board 103 and the body axis direction of the subject M).

An image generation unit 111 is provided at the subsequent stage of the radiation detector 107. Based on the radiation detection signal output from the radiation detector 107, the image generation unit 111 generates a radiation image (two-dimensional image) of a region including a target-of-interest. The reconstruction unit 113 reconstructs a plurality of radiation images generated by the image generation unit 111 to generate a three-dimensional image of the region including the target-of-interest.

In the case of generating a three-dimensional image using the radiographic imaging apparatus 101, the C-shaped arm 109 is made approximately a half turn about the axis of the horizontal axis RB. The radiation source 105 and the radiation detector 107 make approximately a half turn along an arc orbit RC rotating about the axis of the x-direction centered on the region-of-interest Mo of the subject M while maintaining the positional relationship in which the radiation source 105 and the radiation detector 107 are opposed to each other across the top board 103. That is, as shown in FIG. 17 (b), the radiation source 105 rotates from the imaging position indicated by the reference numeral 105a to the imaging position indicated by reference numeral 105c via the imaging position indicated by the reference numeral 105b.

The radiation source 105 irradiates radiation to the subject M in each of the imaging positions 105a to 105c. Based on the radiation detection signal output by the radiation detector 107, the image generation unit 111 acquires a radiation image reflecting the cross-section of the blood vessel 115 in the direction of extension (the long-axis direction of the blood vessel 115). The radiation images obtained in the imaging positions 105a to 105c are denoted as two-dimensional images Pa to Pc, respectively. As shown in FIG. 17 (c), the two-dimensional images Pa to Pc are radiation images captured from various directions around the axis of the body axis direction of the subject M with respect to the stent 119 and the blood vessel 115 which are target-of-interests.

The reconstruction unit 113 reconstructs a series of two-dimensional images Pa to Pc to generate a three-dimensional image T as shown in FIG. 17 (d). The three-dimensional image T reflects three-dimensional image data of the blood vessel 115 having the branched blood vessel 117 and the stent 119. Based on the three-dimensional image T, a radiation image reflecting a cross-section (long-axis cross-section) of the stent 119 in the long-axis direction and a radiation image reflecting a cross-section (short-axis cross-section) of the stent 119 perpendicular to the long-axis cross-section are generated, and these images are displayed in a parallel state.

The radiation image of the long-axis cross-section (long-axis cross-sectional image) is a cross-sectional image perpendicular to the y-direction, and the radiation image of the short-axis cross-section (short-axis cross-sectional image) is a cross-sectional image perpendicular to the x-direction. Therefore, in carrying out the IVR treatment, a surgeon can confirm the precise information of the stent 119 in each of the three-dimensional directions by referring to the long-axis cross-sectional image and the short-axis cross-sectional image which are in a relation of plane images orthogonal to each other.

In recent years, a radiographic imaging apparatus has been reported in which when diagnosing an inside of a tubular body such as a blood vessel or a digestive tract, a virtual endoscope image is generated based on the three-dimensional image information obtained using a radiation image (see, for example, Patent Document 2). When performing a diagnosis by a virtual endoscope image, unlike an ordinary endoscopic diagnosis, the position of the viewpoint with respect to the image can be arbitrarily set. Therefore, an endoscopic observation is performed based on the set viewpoint position, so that a more appropriate diagnosis can be performed.

PRIOR ART

Patent Document

Patent Document 1

Japanese Unexamined Patent Application Publication No. 2005-287524

Patent Document 2

Japanese Unexamined Patent Application Publication No. 2013-27697

SUMMARY OF THE INVENTION

Problems to be Solved by the Invention

However, in the case of the conventional example having such a configuration, there are following problems. That is, in the conventional apparatus, since the calculation to reconstruct the three-dimensional image from the two-dimensional image is complicated, it takes a long time to complete the calculation of the image reconstruction and acquire the three-dimensional image. Therefore, when acquiring a three-dimensional image during an IVR, a surgeon will be kept waiting for a long time until the calculation of the reconstruction is completed and the three-dimensional image is actually acquired. Therefore, the surgeon spends a waste of time during the IVR treatment, so the IVR takes longer to complete. As a result, there is a concern that the burden on the surgeon and the subject increases and the IVR efficiency decreases.

The present invention has been made in view of the aforementioned circumstances, and aims to provide a radiographic imaging apparatus capable of quickly acquiring three-dimensional image data of a target-of-interest when an IVR or the like is performed.

Means for Solving the Problems

In order to attain such an object, the present invention has the following configuration. That is, a radiographic imaging apparatus according to the present invention includes: a radiation source configured to irradiate radiation to a subject; radiation detection means configured to detect the radiation transmitted through the subject; imaging system moving means configured to move an imaging system composed of the radiation source and the radiation detection means along a predetermined orbit with respect to the subject; radiation irradiation control means configured to control to make the radiation source repeat radiation irradiation while the imaging system moves along the predetermined orbit with respect to the subject; image generation means configured to generate a two-dimensional image of a region including a device to be inserted into a body of the subject based on a radiation detection signal output by the radiation detection means each time the radiation source performs radiation irradiation; a region-of-interest extraction means configured to extract a predetermined region including a part of the device as a region-of-interest from each of the two-dimensional images generated by the image generation means; and reconstruction means configured to reconstruct a three-dimensional image of the region-of-interest based on each of images corresponding to the region-of-interest extracted by the region-of-interest extraction means from each of a series of the two-dimensional images generated by the image generation means.

[Functions and Effects] According to the radiographic imaging apparatus according to the present invention, the region-of-interest extraction means extracts a predetermined region including a part of the device as a region-of-interest from each of a series of two-dimensional images. The reconstruction means reconstructs a three-dimensional image of a region-of-interest based on each image of the part corresponding to the region-of-interest. The region-of-interest used to reconstruct the three-dimensional image corresponds to a part of the entire two-dimensional image. That is, there is no need for the reconstruction means to perform a calculation to reconstruct the entire image for the series of two-dimensional images when generating the three-dimensional image. As a result, since the three-dimensional image data can be quickly obtained for the region requiring the reconstruction, the time required for diagnosis can be greatly shortened, which can reduce the burden on a surgeon and a subject.

Further, in the aforementioned invention, the radiographic imaging apparatus preferably further includes: image segmentation means configured to segment a portion of the device from the two-dimensional image to generate a segment image; short-axis cross-sectional image generation means configured to generate a radiation image of a cross-section orthogonal to a long-axis direction of the device as a short-axis cross-sectional image based on the three-dimensional image; and image display means configured to display the segment image and the short-axis cross-sectional image in parallel.

[Functions and Effects] According to the radiographic imaging apparatus of the present invention, it is provided with a short-axis cross-sectional image generation means that generates a radiation image of a cross-section of a device orthogonal to a long-axis direction based on the three-dimensional image as a short-axis cross-sectional image. The image segmentation means segments the part of the device from the two-dimensional image to generate a segment image. The image display means displays the segment image and the short-axis cross-sectional image in parallel.

Each of the two-dimensional images is generated when radiation is irradiated while the imaging system moves along a predetermined orbit with respect to the subject. In other words, each of the two-dimensional images and the short-axis cross-sectional image are different in viewpoint direction. Since two images different in viewpoint direction are displayed in parallel, a surgeon can easily obtain information on the position and the state of the device in each direction of three dimensions by referring to two images displayed in parallel. As a result, it becomes possible to perform the treatment requiring three-dimensional image data quickly and more precisely.

Further, the segment image is generated by segmenting the part of the device from a two-dimensional image. That is, the image of the device reflected in the segment image is higher in visibility than the image of the device reflected in the two-dimensional image. Therefore, a surgeon can confirm more precise information on the position of the device and so on by referring to the segment image.

Further, in the present invention, the radiographic imaging apparatus preferably further includes: feature point extraction means configured to extract a feature point from the two dimensional image; and integrating means configured to generate an integrated image by superimposing a plurality of the two-dimensional images with the feature point extracted by the feature point extraction means as a reference, wherein the image segmentation means segments the portion of the device from the integrated image to generate the segment image.

[Functions and Effects] According to the radiographic imaging apparatus of the present invention, the integrating means superimposes a plurality of two-dimensional images with a feature point as a reference to generate an integrated image. By superimposing a plurality of two-dimensional images, the image of the device reflected in the integrated image further increases in visibility. The image segmentation means segments the portion of the device from the integrated image to generate a segment image, and the image display means displays the segment image segmented from the integrated image and the short-axis cross-sectional image in parallel. Therefore, a surgeon can acquire more precise information of the device by referring to a segment image of the device high in visibility and a short-axis cross-sectional image of the device.

Further, in the aforementioned invention, the radiographic imaging apparatus preferably further includes: region-of-interest display means configured to display a range of the region-of-interest with respect to the segment image to be displayed on the image display means.

[Functions and Effects] According to the radiographic imaging apparatus of the present invention, it is provided with region-of-interest display means configured to display a range of a region-of-interest with respect to a segment image to be displayed on image display means. In this case, a surgeon can easily confirm the portion of the image used to generate the short-axis cross-sectional image in the segment image by referring to the position of the region-of-interest displayed in the segment image. As a result, it is possible to acquire more precise three-dimensional information about the position of the device.

Further, in the aforementioned invention, the radiographic imaging apparatus preferably further includes: region-of-interest setting means configured to arbitrarily set a position and a size of the region-of-interest to be reflected in the segment image, wherein the region-of-interest extraction means extracts an image corresponding to the region-of-interest from each of the two-dimensional images based on the region-of-interest set by the region-of-interest setting means.

[Functions and Effects] According to the radiographic imaging apparatus of the present invention, the region-of-interest setting means arbitrarily sets the position and the size of the region-of-interest to be displayed in the segment image. The region-of-interest extraction means extracts an image corresponding to the region-of-interest from each of the two-dimensional images based on the region-of-interest set by the region-of-interest setting means. In this case, the position and the size of the region-of-interest can be arbitrarily changed as necessary. For this reason, a surgeon can arbitrarily set the region where the surgeon wants to check the short-axis cross-sectional image as a region-of-interest by referring to the segment image. As a result, it is possible to acquire more detailed three-dimensional information on the position and the state of the device.

Further, in the aforementioned invention, the radiographic imaging apparatus preferably further includes: virtual endoscope image generation means configured to generate a virtual endoscope image of the region-of-interest by correcting a size of each of the short-axis cross-sectional images to be generated based on the three-dimensional image so that the size becomes larger as it approaches a viewpoint for the short-axis cross-sectional image and superimposing corrected short-axis cross-sectional images.

[Functions and Effects] According to the radiographic imaging apparatus of the present invention, it is provided with virtual endoscope image generation means configured to generate a virtual endoscope image of a region-of-interest. The virtual endoscope image is generated by correcting a size of each of the plurality of short-axis cross-sectional images to be generated based on the three-dimensional image so that the size becomes larger as it approaches a viewpoint for the short-axis cross-sectional image and superimposing each of the corrected short-axis cross-sectional images.

In this case, in the virtual endoscope image, an image positioned closer to the viewpoint looks larger, and an image positioned distant from the viewpoint looks smaller. Therefore, by referring to the virtual endoscope image, information equivalent to the endoscopic image can be obtained. Therefore, it is possible to generate a virtual endoscope image for the region-of-interest without inserting an endoscope into a subject and perform endoscopic observation on the device.

Also, a virtual endoscope image is generated based on the three dimensional image. That is, the virtual endoscope image is generated not based on the series of the entire two-dimensional images, but based on each of a part of images corresponding to the region-of-interest of the series of the entire two-dimensional images. Therefore, the time required to generate the virtual endoscope image can be shortened. Therefore, it is possible to perform a treatment requiring a virtual endoscope image more rapidly and efficiently.

In the aforementioned invention, it is preferable that the image display means display the segment image and the virtual endoscope image in parallel.

[Functions and Effects] According to the radiographic imaging apparatus of the present invention, the image display means displays the segment image and the virtual endoscope image in parallel. Since the virtual endoscope image is generated by superimposing the short-axis cross-sectional images, the segment image and the virtual endoscope image are different in viewpoint direction. Since two images different in viewpoint direction are displayed in parallel, a surgeon can easily obtain three-dimensional information about the position and the state of the device by referring to two images displayed in parallel. As a result, it becomes possible to perform the treatment requiring three-dimensional image data quickly and more precisely.

Further, in the aforementioned invention, the radiographic imaging apparatus preferably further includes contour display means configured to display a contour of the device reflected in the short-axis cross-sectional image.

[Functions and Effects] According to the radiographic imaging apparatus of the present invention, the contour display means detects the contour of the device reflected in the short-axis cross-sectional image and displays the detected contour in the short-axis cross-sectional image. Therefore, in the short-axis cross-sectional image or the virtual endoscope image, the visibility of the device is further enhanced. Therefore, the three-dimensional information of the device can be more easily confirmed.

Further, in the aforementioned invention, it is preferable that the radiographic imaging apparatus further includes: reference point extraction means configured to extract a reference point from the two dimensional image; and image correction means configured to correct each of a series of the two-dimensional images based on the reference point so that a position of the device reflected in the two-dimensional image is the same, wherein the region-of-interest extraction means extracts an image of a portion corresponding to the region-of-interest from the series of the two-dimensional images corrected by the image correction means.

[Functions and Effects] According to the radiographic imaging apparatus of the present invention, the image correction means corrects each of a series of two-dimensional images based on the reference point so that the position of the device reflected in the two-dimensional image is the same. In this case, even in cases where the position of the device reflected in each of the two-dimensional images is different, the position of the device reflected in each two-dimensional image becomes the same by the image correction means. Since the image correction means corrects the two-dimensional image based on the reference point, the position adjustment of the device in the two-dimensional image is performed accurately.

Therefore, in the three-dimensional image generated by reconstructing the corrected two-dimensional image, an image of the device high in contrast can be obtained. Therefore, even when the device is moving at high speed as occasionally due to the heartbeat, etc., such as during an IVR treatment, it is possible to acquire a high-quality three-dimensional image showing the region including the device in real time. A surgeon can perform an IVR with higher accuracy by using the high quality three-dimensional image reflecting the device.

Effects of the Invention

According to the radiographic imaging apparatus according to the present invention, the region-of-interest extraction means extracts a predetermined region including a part of the device as a region-of-interest from each of a series of two-dimensional images. The reconstruction means reconstructs a three-dimensional image of a region-of-interest based on each image of the part corresponding to the region-of-interest. The region-of-interest used to reconstruct the three-dimensional image corresponds to a part of the entire two-dimensional image. That is, there is no need for the reconstruction means to perform a calculation to reconstruct the entire image for the series of two-dimensional images when generating the three-dimensional image. As a result, since three-dimensional image data can be quickly obtained for the region requiring the reconstruction, the time required for diagnosis can be greatly shortened, which can reduce the burden on a surgeon and a subject.

EMBODIMENTS FOR CARRYING OUT THE INVENTION

Example 1

Figure 1:
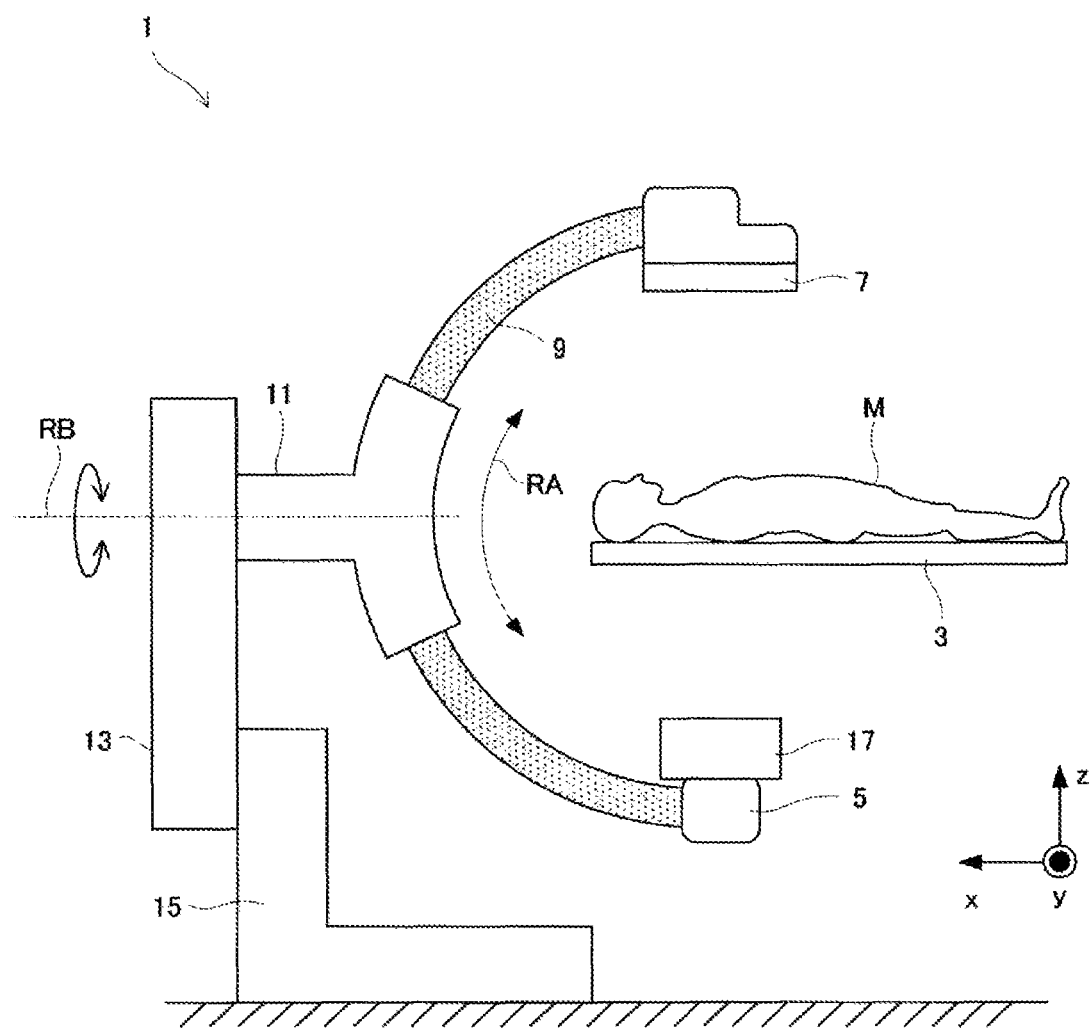
FIG. 1 is a front view illustrating a schematic configuration of a radiographic imaging apparatus according to Example 1.

Hereinafter, Example 1 of the present invention will be described with reference to the attached drawings. As an example of radiation, the description will be made using an X-ray. FIG. 1 is a schematic diagram illustrating a configuration of a radiographic imaging apparatus according to Example 1.

Description of Operation

The radiographic imaging apparatus 1 according to Example 1 is equipped with a top board 3 for placing a subject M taking a horizontal posture thereon, an X-ray tube 5 for irradiating an X-ray to the subject M, and an X-ray detector 7 for detecting the X-ray emitted from the X-ray tube 5 and converting it to an electric signal. The X-ray tube 5 and the X-ray detector 7 are arranged so as to oppose to each other across the top board 3. The X-ray tube 5 and the X-ray detector 7 constitute an imaging system.

The X-ray detector 7 is provided with a detection surface for detecting an X-ray. On the detection surface, pixels which are X-ray detection elements are arranged in a two-dimensional matrix of about 4,096 vertical lines×4,096 horizontal lines. In Example 1, a flat panel type detector (FPD) is used as the X-ray detector 7. Note that the X-ray tube 5 corresponds to the radiation source in the present invention, and the X-ray detector 7 corresponds to the radiation detection means in the present invention.

The X-ray tube 5 and the X-ray detector 7 are provided at one end of a C-shaped arm 9 and the other end thereof, respectively. The C-shaped arm 9 is held by an arm holding member 11 and configured to slidably move along the circular arc path of the C-shaped arm 9 indicated by the reference symbol "RA". The arm holding member 11 is arranged on the side surface of the support post 13 and configured to be rotatable about the axis of the horizontal axis RB parallel to the x-direction (the longitudinal direction of the top board 3 and the body axis direction of the subject M). The C-shaped arm 9 held by the arm holding member 11 rotatably move about the axis of the x-direction in accordance with the arm holding member 11.

The support post 13 is supported by a support base 15 disposed on the floor surface, and is configured so as to be horizontally movable in the y-direction (in the short direction of the top board 3). The arm supporting member 11 and the C-shaped arm 9 supported by the support post 13 move in the y-direction in accordance with the horizontal movement of the support post 13. The collimator 17 is provided on the X-ray tube 5, and limits the X-ray irradiated from the X-ray tube 5 to, for example, a fan shape of a fan angle θ.

Figure 2:
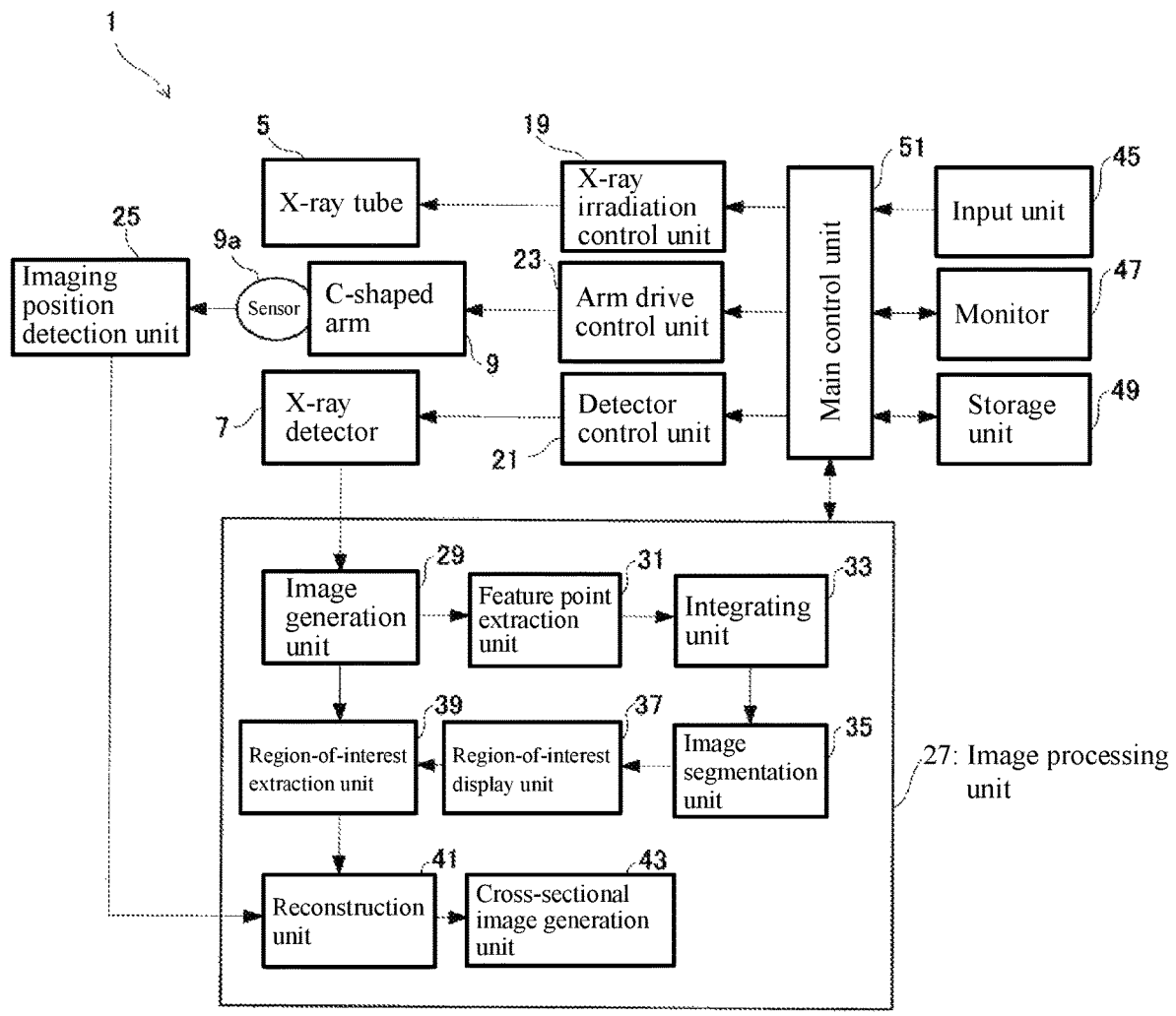
FIG. 2 is a functional block diagram illustrating the configuration of the radiographic imaging apparatus according to Example 1.

Here, the configuration of the radiographic imaging apparatus 1 will be described in more detail. As shown in FIG. 2, the radiographic imaging apparatus 1 is equipped with an X-ray irradiation control unit 19, a detector control unit 21, an arm drive control unit 23, an imaging position detection unit 25, and an image processing unit 27.

The X-ray irradiation control unit 19 is configured to output a high voltage to the X-ray tube 5. Based on the high voltage output given by the X-ray irradiation control unit 19, the X-ray dose that the X-ray tube 5 irradiates and the timing when an X-ray is irradiated are controlled. The detector control unit 21 controls the operation of reading out the charge signal converted by the X-ray detector 7, that is, the X-ray detection signal.

The arm drive control unit 23 controls the sliding movement of the C-shaped arm 9. As the C-shaped arm 9 slides in the direction indicated by the symbol "RA", the spatial position of each of the X-ray tube 5 and the X-ray detector 7 changes while maintaining the opposed arrangement state. Further, the arm drive control unit 23 totally controls the rotational movement of the arm supporting member 11 in addition to the sliding movement of the C-shaped arm 9. Since the X-ray tube 5 and the X-ray detector 7 are mounted on the C-shaped arm 9, each spatial position changes while maintaining the opposed arrangement state in accordance with the rotational movement of the arm supporting member 11. Note that the arm drive control unit 23 corresponds to the imaging system moving means in the present invention.

The slide movement amount of the C-shaped arm 9 and the rotational movement amount of the arm supporting member 11 are detected by a plurality of sensors 9a attached to the C-shaped arm 9 and the arm supporting member 11. Each detection signal of the sensor 9a is transmitted to the imaging position detection unit 25. Based on each detection signal, the imaging position detection unit 25 detects the position information of the imaging system composed of the X-ray tube 5 and the FPD 7. In addition, the imaging position detection unit 25 detects the direction of the central axis (X-ray irradiation axis direction) of an X-ray irradiated from the X-ray tube 5 based on each detection signal.

The image processing unit 27 is provided with an image generation unit 29, a feature point extraction unit 31, an integrating unit 33, an image segmentation unit 35, a region-of-interest display unit 37, a region-of-interest extraction unit 39, a reconstruction unit 41, and a cross-sectional image generation unit 43. The image generation unit 29 is provided at the subsequent stage of the X-ray detector 7, and generates an X-ray image (two-dimensional image) reflecting a region including a target-of-interest of the subject M based on the X-ray detection signal output from the X-ray detector 7. The image generation unit 29 corresponds to the image generation means according to the present invention.

The feature point extraction unit 31 is provided at the subsequent stage of the image generation unit 29, and extracts a feature point from each of the two-dimensional images generated by the image generation unit 29. The integrating unit 33 integrates and superimposes a plurality of two-dimensional images with the feature point extracted by the feature point extraction unit 31 as a reference and generates an integrated image. The image segmentation unit 35 generates a segment image by segmenting an image of the target-of-interest and the vicinity of the target-of-interest reflected in the integrated image and appropriately rotating and/or enlarging it. Note that the feature point extraction unit 31 corresponds to the feature point extraction means and the reference point extraction means according to the present invention. Also note that the integrating unit 33 corresponds to the integrating means in the present invention. The image segmentation unit 35 corresponds to the image segmentation means in the present invention.

The region-of-interest display unit 37 displays the information indicating a predetermined region (region-of-interest) set by an input unit 45 which will be described later and information indicating each of the position and the direction of the viewpoint with respect to the region-of-interest on a segment image. The region-of-interest extraction unit 39 extracts an image of a region corresponding to a region-of-interest from each of the two-dimensional images generated for one scan. Note that one scan means X-ray irradiation performed while the C-shaped arm 9 rotates by a predetermined angle about the axis of the horizontal axis RB. Note that the region-of-interest display unit 37 corresponds to the region-of-interest display means in the present invention, and the region-of-interest extraction unit 39 corresponds to the region-of-interest extraction means in the present invention.

The reconstruction unit 41 reconstructs each image of the region-of-interest extracted by the region-of-interest extraction unit 39 and generates a three-dimensional image showing a region including the target-of-interest. The cross-sectional image generation unit 43 generates an X-ray image in an arbitrary cross-section of the three-dimensional image based on the three-dimensional image reconstructed by the reconstruction unit 41. As an example of the X-ray image generated by the cross-sectional image generation unit 43, an X-ray image of a cross-section orthogonal to the two-dimensional image, that is, an X-ray image in a cross-section perpendicular to the long-axis direction of the stent which will be described later (short-axis cross-sectional image) can be exemplified. Note that the reconstruction unit 41 corresponds to the reconstruction means in the present invention. Also note that the cross-sectional image generation unit 43 corresponds to the short-axis cross-sectional image generation unit in the present invention.

The radiographic imaging apparatus 1 is further provided with an input unit 45, a monitor 47, a storage unit 49, and a main control unit 51. The input unit 45 is for inputting an instruction of a surgeon, and can be exemplified by, for example, a mouse input type or a keyboard input type panel, a touch input type panel, and the like. The input unit 45 has a configuration of setting a region for executing the reconstruction of three-dimensional image of the two-dimensional image as a region-of-interest. The monitor 47 displays various images, such as, e.g., a two-dimensional image, a three-dimensional image, and a short-axis cross-sectional image. The monitor 47 also has a configuration for displaying a plurality of types of images in a manner arranged in parallel.

The storage unit 49 stores various images generated by, e.g., the image generation unit 29 or the reconstruction unit 41, the position of each of the imaging systems, and various kinds of information on the X-ray irradiation axis direction of the X-ray tube 5. The main control unit 51 totally controls each of the X-ray irradiation control unit 19, the detector control unit 21, the arm drive control unit 23, the image processing unit 27, the monitor 47, and the storage unit 49. Note that the input unit 45 corresponds to the region-of-interest setting means in the present invention, and the monitor 47 corresponds to the image display means in the present invention.

Figure 3:
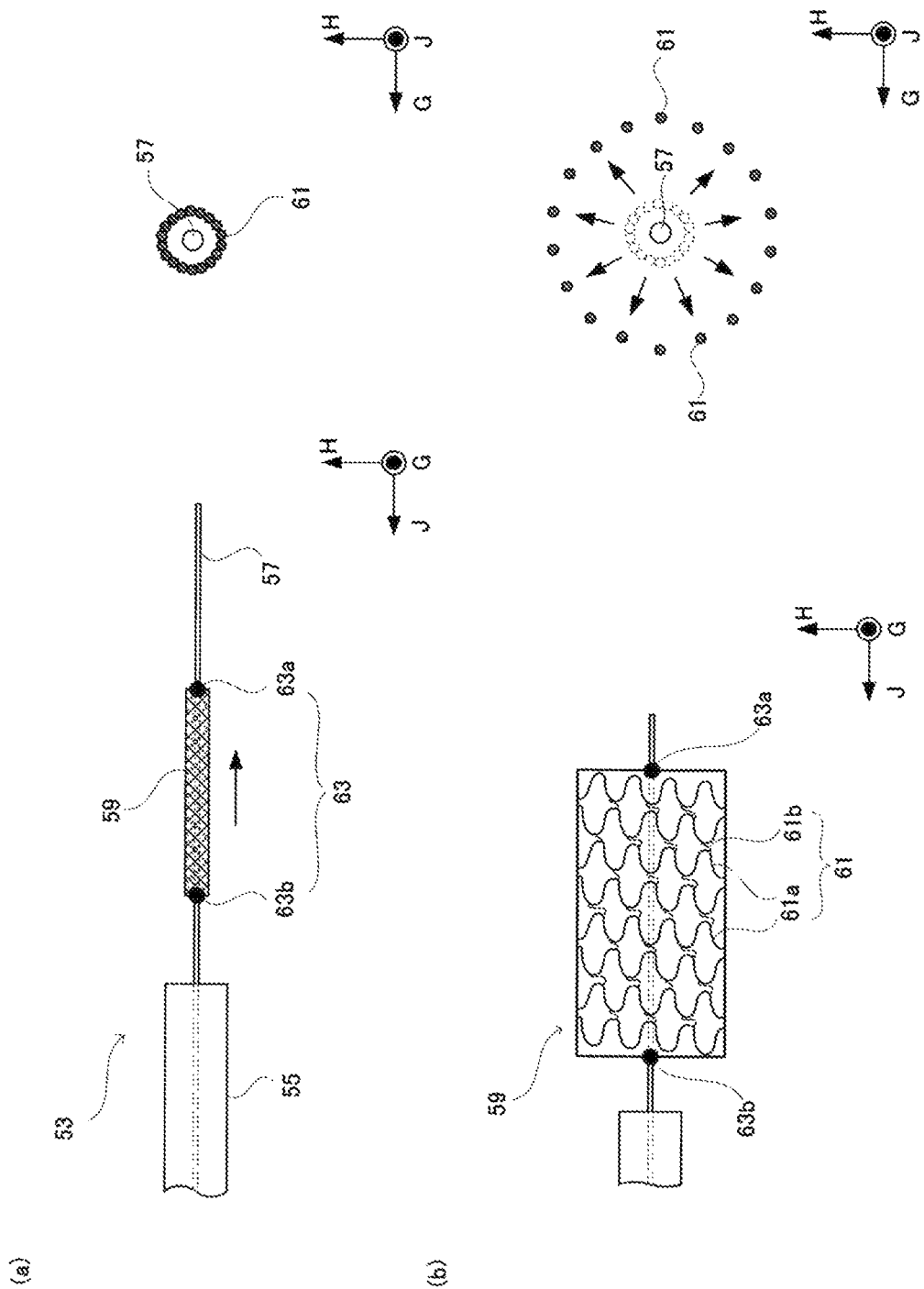
FIG. 3 is a schematic diagram illustrating a configuration of a catheter system according to Example 1. (a) is a diagram of the catheter system in the case where the stent is in a non-expanded state, and (b) is a diagram of the catheter system in the case where the stent is in an expanded state.

FIG. 3 is a schematic diagram showing the configuration of a catheter system 53 used for an interventional treatment. The catheter system 53 is equipped with a catheter 55, a guide wire 57, and a stent 59. The guide wire 57 is passed through the inside of the tubular catheter 55. The stent 59 is provided inside the catheter 55 and has a configuration capable of being moved in the direction indicated by the arrow along the guide wire 57. Note that the stent 59 corresponds to the device in the present invention.

The stent 59 is a member formed in a cylindrical shape with a mesh using a strut 61 having a structure like a wire, and a balloon (not shown) is provided inside. In an IVR, the stent 59 in a non-expanded state shown in FIG. 3 (*a*) is placed in a stenosed position of a blood vessel. Then, the arranged stent 59 is expanded by a balloon into an expanded state shown in FIG. 3 (*b*). By placing the stent 59 in the expanded state in the blood vessel, it is possible to expand the stenosed segment to keep the blood flow normal.

The strut 61 is made of a metal wire material, such as, e.g., stainless steel. The strut 61 is constituted by a plurality of waveform struts 61*a* arranged at intervals in the long-axis direction (J-direction) of the stent 59 and a connection strut 61*b* connecting adjacent waveform struts 61*a*. Such a configuration is an example of the configuration pattern of the strut 61 and may be changed arbitrary. The direction orthogonal to the long-axis direction is defined as a short-axis direction. As an example of the short-axis direction, the G-direction corresponding to the depth direction of the stent 59 and the H-direction corresponding to the height direction of the stent 59 as shown in FIG. 3 can be exemplified.

The stent 59 is provided with a plurality of markers 63. In Example 1, the number of markers 63 is two, but the number of markers 63 may be changed as required. Of the two markers 63, one of the markers 63*a* is provided on the tip end side of the stent 59 in the long-axis direction, and the other of the markers 63*b* is provided on the base end side of the stent 59 in the long-axis direction. Each of the markers 63 is made of a radiopaque material, and specifies the position of the stent 59 in the X-ray image. As an example of the material constituting the marker 63, gold, platinum, and tantalum, can be exemplified. Note that the stent 59 corresponds to the device in the present invention. Note that the marker 63 corresponds to the feature point and the reference point in the present invention.

Description of Operation

Figure 4:
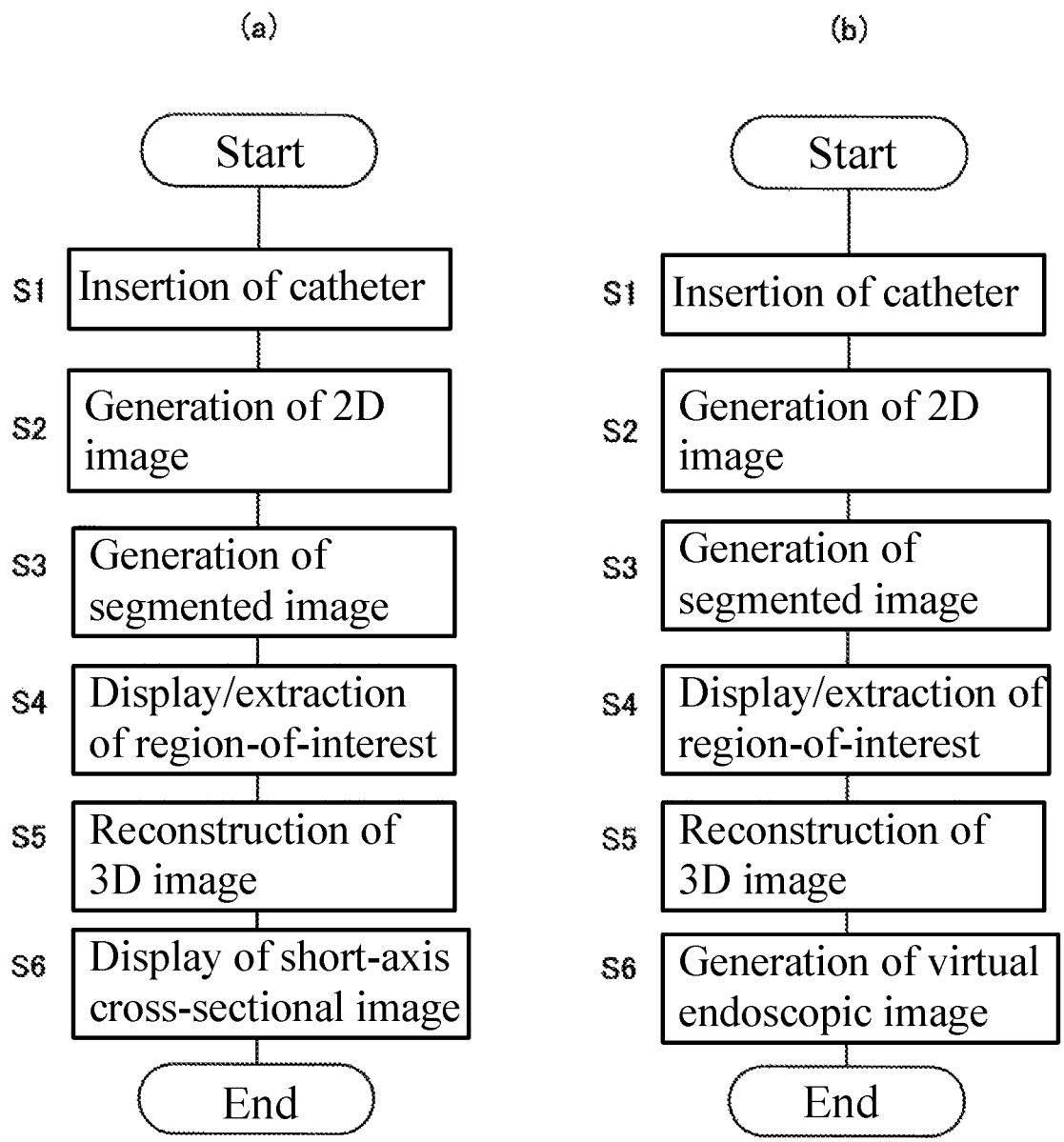
FIG. 4 (*a*) is a flowchart describing steps of the operation in Example 1, and FIG. 4 (*b*) is a flowchart describing steps of the operation in Example 2.

Next, the operation of the radiographic imaging apparatus 1 according to Example 1 will be described. FIG. 4 illustrates flowcharts describing the operation of the radiographic imaging apparatus according to Example 1. Here, a case in which an IVR is performed using the radiographic imaging apparatus will be described as an example. The description will be made considering the stent 59 as a target-of-interest.

Step S1 (Insertion of Catheter)

Figure 5:
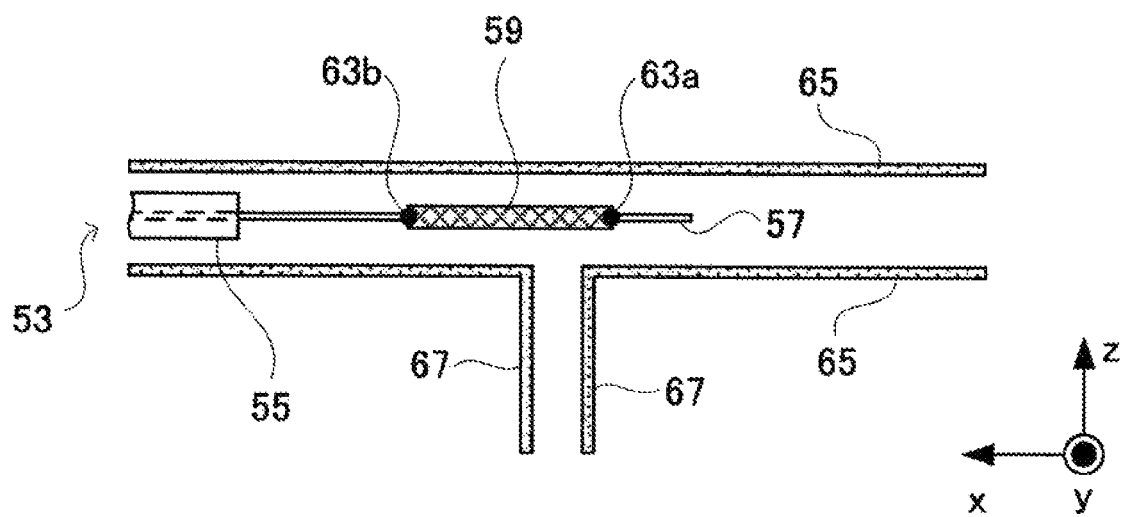
FIG. 5 is a schematic diagram illustrating a positional relationship of the catheter system according to Example 1 in a blood vessel.

In performing an IVR, initially, a subject M is placed on the top board 3 as shown in FIG. 1. Then, a surgeon opens a small hole, for example, in the base of the upper leg of the subject M and inserts the catheter system 53 into the blood vessel. In FIG. 5, a state is shown in which the stent 59 is inserted into the blood vessel 65 together with the catheter 55 and the guide wire 57 with respect to the blood vessel 65 having a branched blood vessel 67. For convenience of explanation, it is assumed that the blood vessel 65 extends in the x-direction (the longitudinal direction of the top board 3 and the body axis direction of the subject M), and the branched blood vessel 67 extends downward from the blood vessel 65 in the z-direction (vertical direction). It is also assumed that the long-axis direction (J-direction) of the inserted stent 59 coincides with the x-direction.

Step S2 (Generation of Two-dimensional Image)

After inserting the catheter system 45 into the blood vessel of the subject M, a two-dimensional image is generated. The two-dimensional image generated in Step S2 is used for generating a three-dimensional image which will be described later. The surgeon operates the input unit 45 to continuously perform the X-ray fluoroscopy while making the arm holding member 11 approximately a half turn about the axis of the horizontal axis RB parallel to the x-direction. The predetermined angle at which the arm holding member 11 is actually rotated is preferably an angle (about 200°) obtained by adding the fan angle θ to 180°. The imaging system composed of the X-ray tube 5 and the X-ray detector 7 moves along the arc orbit rotating about the body axis of the subject M (about the axis of the x-direction) in accordance with the arm holding member 11 while keeping the positional relationship in which the X-ray tube 5 and the X-ray detector 7 are opposed to each other across the top board 3.

Figure 6:
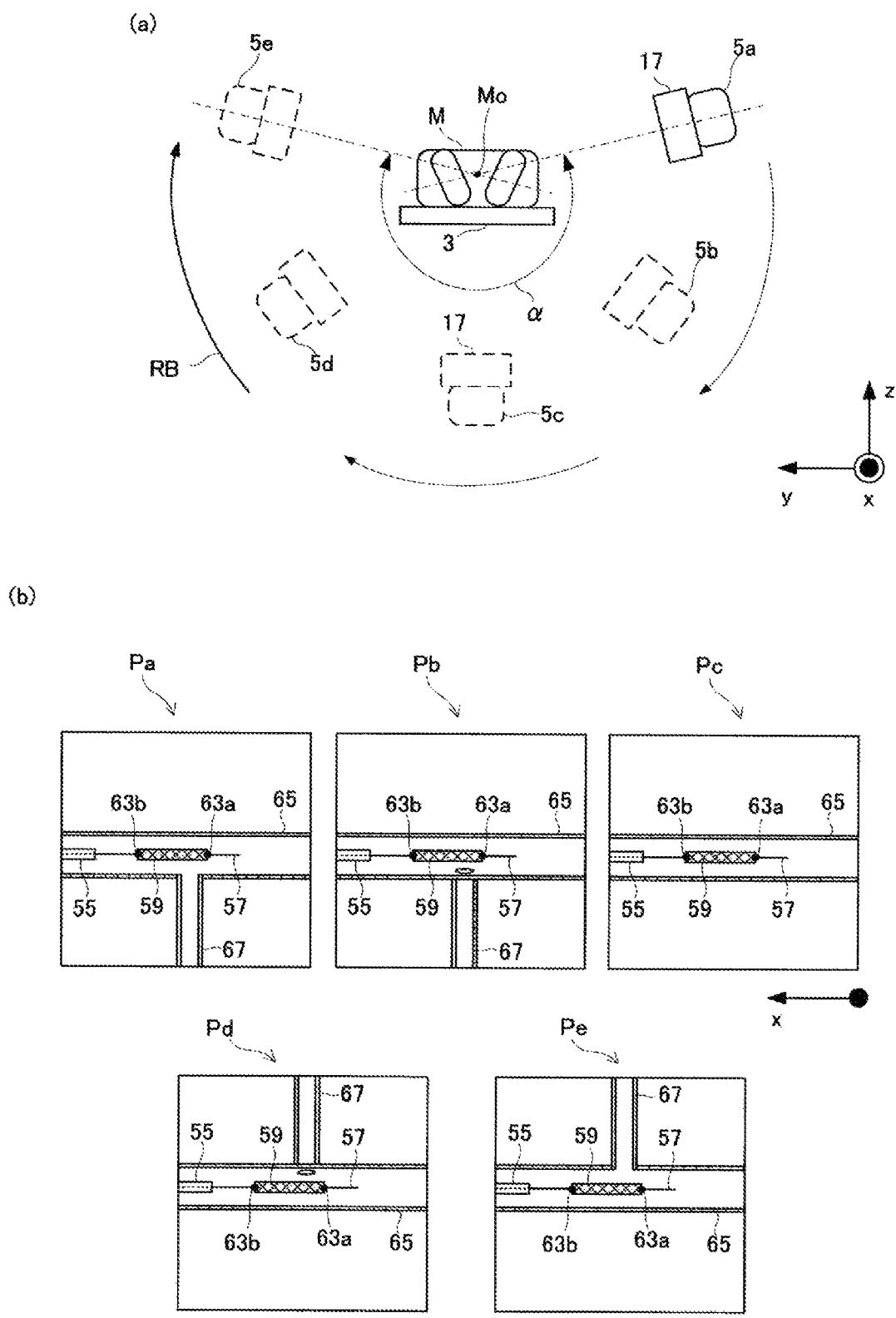
FIG. 6 is a diagram describing a step of Step S2 according to Example 1. (a) is a diagram illustrating each imaging position in one scan, and (b) is a diagram illustrating two-dimensional images generated in each imaging position.

Here, the operation of the X-ray tube 5 will be specifically described with reference to FIG. 6. FIG. 6 (a) is a view of the radiographic imaging apparatus 1 viewed from the foot side of the subject M in the x-direction. For convenience of explanation, in FIG. 6 (a), the X-ray detector 7 and the like are omitted, and the positional relationship between the subject M and the X-ray tube 5 is illustrated.

The X-ray tube 5 moves along the arc orbit RC which rotates approximately half turn about the axis of the x-direction centering on the region-of-interest Mo. In other words, the X-ray tube 5 rotates from the imaging position indicated by the reference numeral 5a to the imaging position indicated by the reference numeral 5e while sequentially passing through the imaging positions indicated by the reference numerals 5b to 5d. In Example 1, the angle a at which the X-ray tube 5 rotates from the imaging position 5a to the imaging position 5e is an angle obtained by adding the fan angle θ to 180°. In Example 1, the irradiation of the X-ray performed while the X-ray tube 5 rotates from the reference numeral 5a to the reference numeral 5e is defined as one scan.

While the X-ray tube 5 moves from the imaging position 5a to the imaging position 5e, the X-ray tube 5 intermittently irradiates a low dose X-ray to the subject M. Generally, the number of times of X-ray irradiation in one scan is several tens of times. For convenience of explanation, in Example 1, it is assumed that the X-ray tube 5 irradiates an X-ray once in each of the five imaging positions indicated by the reference numerals 5a to 5e. The position and the number of times the X-ray tube 5 irradiates an X-ray in one scan may be appropriately changed according to the conditions.

The X-ray that has passed through the subject M is detected by the X-ray detector 7. The detected X-ray is converted into an X-ray detection signal which is an electric signal, and the X-ray detection signal is output to the image generation unit 29. Based on the output X-ray detection signal, the image generation unit 29 intermittently generates a two-dimensional image P reflecting the stent 59, the blood vessel 65, etc. Note that the two-dimensional image P generated by irradiating the X-ray in each of the imaging positions 5a, . . . , 5e is referred to as a two-dimensional image Pa, . . . , Pe. Therefore, in Example 1, five two-dimensional images P are generated during one scan.

As shown in FIG. 6 (b), the two-dimensional images Pa to Pe are X-ray images captured from various directions around the x-direction axis with respect to the stent 59 as a target-of-interest. The two-dimensional image Pa and the two-dimensional image Pe are images obtained by capturing the image of the target-of-interest in a substantially horizontal direction and the two-dimensional image Pc is an image obtained by capturing the image of the target-of-interest from the vertical direction. That is, each of the two-dimensional images Pa to Pe is an X-ray image (long-axis cross-sectional image) which reflects a cross-section of the stent 59 parallel to each of the long-axis directions.

In generating each of the two-dimensional images P, the imaging position detection unit 25 detects the position of the imaging system and the X-ray irradiation axis direction of the X-ray tube 5 at needed. The information on the position of the imaging system and the information on the X-ray irradiation axis direction detected for each of the two-dimensional images P are transmitted to the reconstruction unit 41, respectively, and used for reconstructing a three-dimensional image. In this way, a series of two-dimensional images Pa to Pe captured at various positions in the arc orbit rotating about the axis of the x-direction is generated. Each of the two-dimensional images Pa to Pe generated in the image generation unit 29 is transmitted to the feature point extraction unit 31.

Step S3 (Generation of Segment Image)

The feature point extraction unit 31 extracts the marker 63 as a feature point from each of the transmitted two-dimensional images Pa to Pe. Since each marker 63 is made of a radiopaque material, the visibility in the two-dimensional image is higher than that of the stent 59 and the blood vessel 65. For this reason, the feature point extraction unit 31 can extract the marker 63 accurately. Each of the two-dimensional images Pa to Pe in which the marker 63 is extracted as a feature point is transmitted from the feature point extraction unit 31 to the integrating unit 33.

The integrating unit 33 selects a predetermined number of images from the most recently generated images among a series of two-dimensional image P from which each marker 63 was extracted. The integrating unit 33 integrates and superimposes the selected two-dimensional images P to generate an integrated image Q. The number of two-dimensional images P used for generating the integrated image Q is, for example, eight, but the number of two-dimensional images P to be superimposed may be changed as appropriate.

Figure 7:
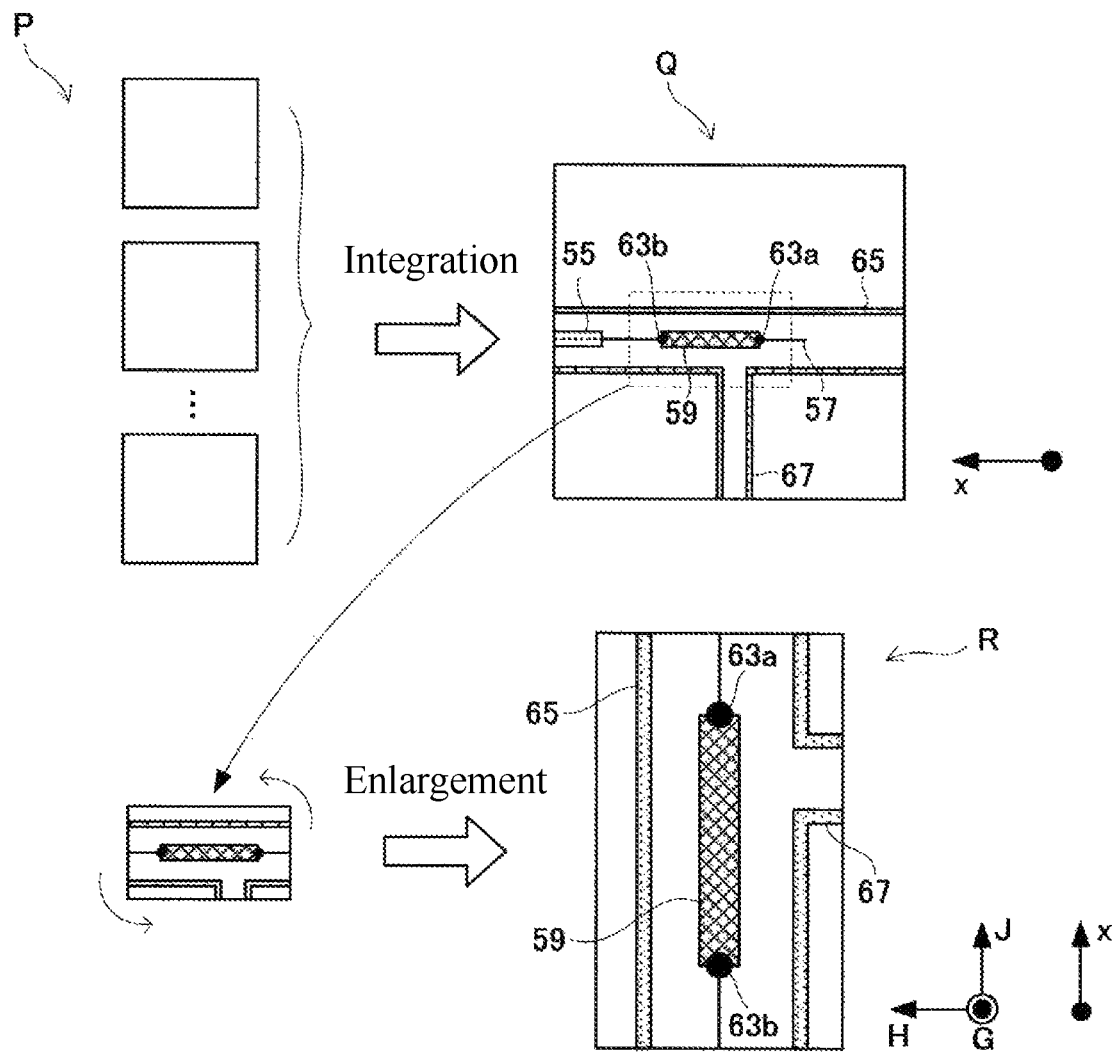
FIG. 7 is a diagram describing a step of Step S3 according to Example 1. The upper figure shows the step of generating an integrated image by superimposing two-dimensional images, and the lower figure shows the step of generating a segment image by rotating/enlarging an image segmented from the integrated image.

At this time, the integrating unit 33 superimposes the two-dimensional images P on the basis of each of the markers 63 to generate an integrated image Q (FIG. 7, upper right). By using the marker 63 as a reference, the position adjustment of the stent 59 reflecting in each of the two-dimensional images P is performed, so that the stent 59 is reflected as a high visibility image in the integrated image Q. Since the integrating unit 33 integrates using the most recently generated two-dimensional images P, the integrated image Q is an X-ray image reflecting the real-time image of the stent 59. The generated integrated image Q is transmitted from the integrating unit 33 to the image segmentation unit 35.

The image segmentation unit 35 segments the image of the stent 59 and its neighboring region from the integrated image Q and appropriately rotates the segmented image (see FIG. 7, lower left). Specifically, with respect to the stent 59, it is preferable to rotate the segmented image such that the marker 63a is positioned at the upper center of the image and the marker 63b is positioned at the lower center of the image. Further, the image segmentation unit 35 appropriately enlarges the rotated image to generate a segment image R (see FIG. 7, lower right). The generated segment image R is transmitted to the region-of-interest display unit 37 and displayed on the monitor 47.

Step S4 (Setting of Region-of-Interest)

Figure 8:
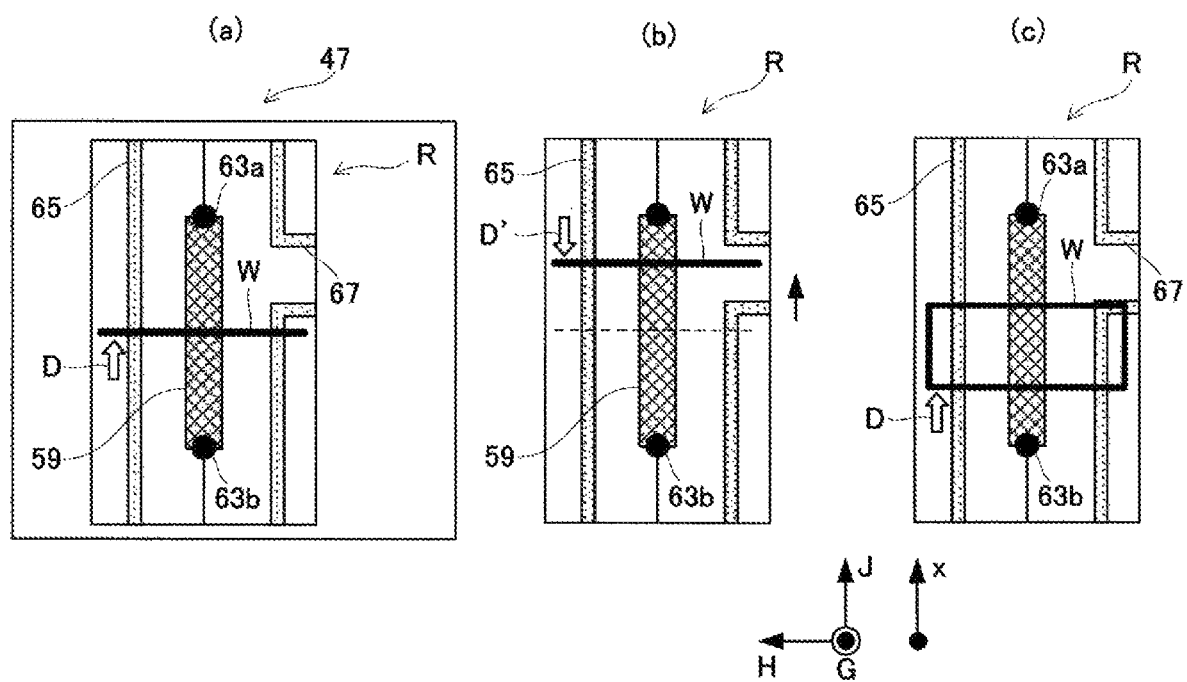
FIG. 8 is a diagram illustrating the step of Step S4 according to Example 1. (a) is a diagram showing a segment image in which a region-of-interest is superimposed and displayed, (b) is a diagram showing a state in which the region-of-interest has moved in parallel, and (c) is a diagram showing a state in which the range of the region-of-interest is enlarged.

A surgeon refers to the segment image R displayed on the monitor 47 and sets a predetermined region including a part of the stent 59 as a region-of-interest. The region-of-interest means a predetermined region in which a three-dimensional image is reconstructed among the long-axis cross-sectional image (image in a cross-section along the J-direction) reflected in the segment image R. As shown in FIG. 8 (a), the region-of-interest W is a rectangular region passing through the middle point between the marker 63a and the marker 63b, and the longitudinal direction of the region-of-interest W extends in the short-axis direction of the stent 59. In order to effectively carry out the interventional treatment, the length of the region-of-interest in the longitudinal direction is preferably about 4 mm. For the purpose of quickly generating a three-dimensional image, it is preferable that the short directional length of the region-of-interest W be a length corresponding to from one pixel to several pixels in the segment image R.

The position and the range of the above-mentioned region-of-interest W are one example of the region-of-interest W in the initial state, and a surgeon can change the position and the size of the region-of-interest W appropriately by manipulating a mouse, a touch panel, etc., provided in the input unit 45. That is, the region-of-interest display unit 37 translates the position of the region-of-interest W as shown in FIG. 8 (b) in accordance with the input instruction. Alternatively, as shown in FIG. 8 (c), the range of the region-of-interest W is enlarged/reduced.

Also, a surgeon operates the input unit 45 to set the viewpoint position and the viewpoint direction in the short-axis cross-sectional image to be generated later. The region-of-interest display unit 37 displays the viewpoint information indicating the position and the direction of the viewpoint on the segment image R according to the input instruction. As an example of the viewpoint information, an arrow indicated by the reference symbol D in FIG. 8 (a) can be exemplified. In this case, the viewpoint direction with respect to the short-axis cross-sectional image is a direction from the marker 63b to the marker 63a. In this case, the viewpoint position is a predetermined position set by a surgeon on the side of the marker 63a from the region-of-interest W. Hereinafter, the viewpoint position will be omitted in the drawing.

Conversely, when the viewpoint direction is a direction from the marker 63b to the marker 63a, the arrow D' as shown in FIG. 8 (b) is displayed on the marker 63a side of the region-of-interest W. In this case, the viewpoint position is a predetermined position on the side of the marker 63a from the region-of-interest W. Each of the information on the region-of-interest W and the viewpoint information is transmitted to the region-of-interest extraction unit 39.

Step S5 (Reconstruction of Three-Dimensional Image)

After setting the region-of-interest W and the arrow D, the reconstruction of a three-dimensional image is executed.

Figure 9:
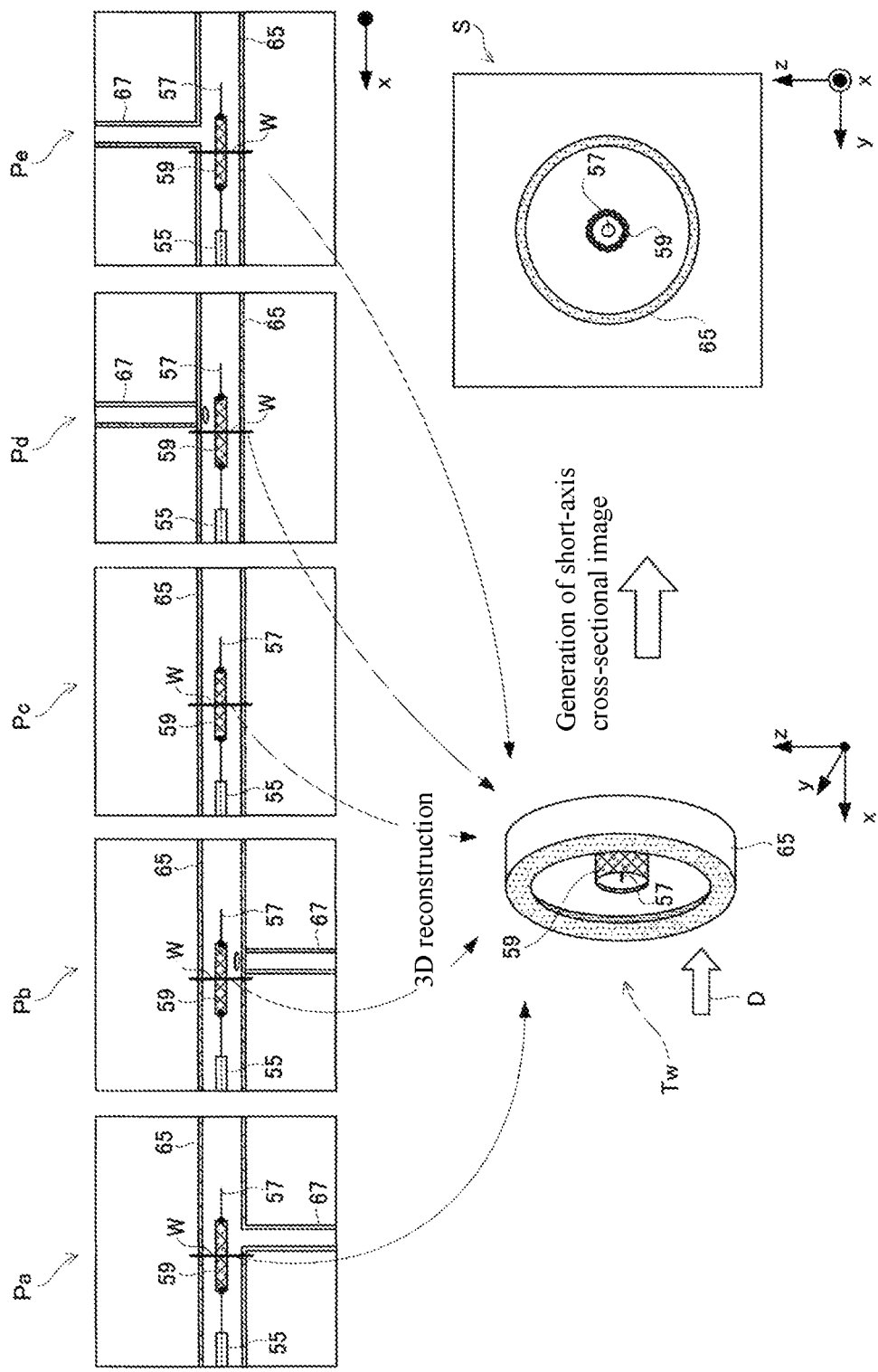
FIG. 9 is a diagram illustrating the step of Step S5 according to Example 1. The upper row illustrates each two-dimensional image in which the region-of-interest is displayed, the left side of the lower row illustrates the three-dimensional image generated by reconstructing the region-of-interest of the two-dimensional image , and the right side of the lower row illustrates a short-axis cross-sectional image generated based on the three-dimensional image.

That is, the region-of-interest extraction unit 39 extracts the image of the region corresponding to the region-of-interest W from each of the intermittently generated two-dimensional images P according to the information on the position and the range of the region-of-interest W (see FIG. 9, upper part). The image of the region-of-interest W in each of the two-dimensional images Pa to Pe is referred to as an images Wa to We, respectively. Each of the extracted images Wa to We is sequentially transmitted to the reconstruction unit 41.

The reconstruction unit 41 reconstructs the three-dimensional image Tw by using each of the images Wa to We of the region-of-interest W extracted from each of the two-dimensional images Pa to Pe. The three-dimensional image Tw is a three-dimensional image reflecting the stent 59, the blood vessel 65, etc., included in the region-of-interest W (see the lower left in FIG. 9). As an example of a configuration for generating a three-dimensional image Tw, a three-dimensional reconstruction algorithm using a filtered back projection method (FBP: Filtered Back Projection) or a successive approximation method can be exemplified.

From the imaging position detection unit 25 to the reconstruction unit 41, the information on the position of the imaging system detected for each of the two-dimensional images Pa to Pe and the information on the X-ray irradiation axis direction of the X-ray tube 5 are transmitted. The reconstruction unit 41 correlates each of the images extracted from the two-dimensional images Pa to Pe with the position information on the imaging system corresponding to each two-dimensional image P and the information on the X-ray irradiation axis direction. The reconstruction unit 41 generates a three-dimensional image Tw by reconstructing each image of the region-of-interest W extracted from the two-dimensional images Pa to Pe based on the correlated information. The generated three-dimensional image Tw is displayed on the monitor 47.

By reconstructing a plurality of images P including an image of the stent 59, the same effect as that obtained when overlapping the images of the stent 59 can be obtained. Therefore, the visibility of the stent 59 reflected in the three-dimensional image Tw is higher than the visibility of the stent 59 reflected in each two-dimensional image P. The image data of the three-dimensional image Tw is transmitted to the cross-sectional image generation unit 43.

The reconstruction unit 41 sequentially performs reconstruction processing using the images sequentially transmitted according to the rotation imaging of the imaging system and sequentially displays the reconstruction images generated by the reconstruction processing. That is, after the two-dimensional image Pa is generated in the imaging position 5a, an image Wa of the region-of-interest W is extracted by the region-of-interest extraction unit 39 and transmitted to the reconstruction unit 41. While the image Wa is extracted and transmitted, the imaging system moves to the imaging position 5b by the rotational movement of the C-shaped arm 9 and capturing the two-dimensional image Pb. As described above, images Wa to We are sequentially extracted and sequentially transmitted to the reconstruction unit 41 during the rotation imaging of the imaging system.

The reconstruction unit 41 sequentially performs reconstruction processing using the image sequentially transmitted to the reconstruction unit 41 among the images Wa to We. As an example, the image Wa and the image Wb are transmitted to the reconstruction unit 41, and at the time when each of the imaging systems is imaging the two-dimensional image Pc at the imaging position 5c, the reconstruction unit 41 performs reconstruction of the three-dimensional image Tw based on the information of the image Wa and the image Wb, and further displays the three-dimensional image Tw on the monitor 47 in real time.

When it becomes a state in which the reconstruction unit 41 extracts the image Wc from the two-dimensional image Pc and sends it to the reconstruction unit 41 and each of the imaging systems moves to the imaging position 5*d* from the imaging position 5*c*, the reconstruction unit 41 reconstructs the three-dimensional image Tw using the images Wa to Wc and displays the generated three-dimensional image Tw in real time. By sequentially processing the images sequentially transmitted according to the rotation imaging of the imaging system as described above, the three-dimensional image is sequentially reconstructed in real time while the imaging system sequentially moves to each imaging position.

In this way, the reconstruction unit 41 does not perform the reconstruction processing until all of the images Wa to We are obtained, but sequentially performs the reconstruction processing using the images sequentially transmitted to the reconstruction unit 41. Therefore, a surgeon will not have to idly wait until the rotation imaging completes and all of the two-dimensional images Pa to Pe are generated. That is, a surgeon can confirm the information of the three-dimensional image Tw which is gradually reconstructed during the execution of the rotation imaging with the monitor 47. Then, at the time when the two-dimensional image Pe is generated, the three-dimensional image Tw based on the images Wa to Wd has already been reconstructed. Accordingly, by extracting and transmitting the image We, the three-dimensional image Tw based on all of the images Wa to We can be promptly reconstructed, so that three-dimensional image Tw is completed almost at the same time as the rotation imaging of the imaging system is completed. As a result, the time required to complete the three-dimensional image Tw can be further shortened.

Step S6 (Display of Short-Axis Cross-Sectional Image)

The cross-sectional image generation unit 43 generates a short-axis cross-sectional image using the three-dimensional image Tw. The short-axis cross-sectional image is a cross-sectional view of the three-dimensional image Tw on a plane (GH-plane) orthogonal to the long-axis direction (J-direction) of the stent 59. The J-direction can be accurately calculated based on the information on the stent 59 and the marker 63 reflected in each of the two-dimensional images P. In Example 1, the J-direction is parallel to the x-direction, so the plane orthogonal to the J-direction is the yz-plane. That is, the cross-sectional image generation unit 43 generates a short-axis cross-sectional image S on the GH-plane based on the viewpoint direction indicated by the arrow D (see the lower right in FIG. 9). As a result, the short-axis cross-sectional image S becomes an X-ray image including the images of the stent 59 and the blood vessel 65 when viewing the three-dimensional image Tw from the viewpoint position (not shown) in the direction indicated by the arrow D.

Figure 10:
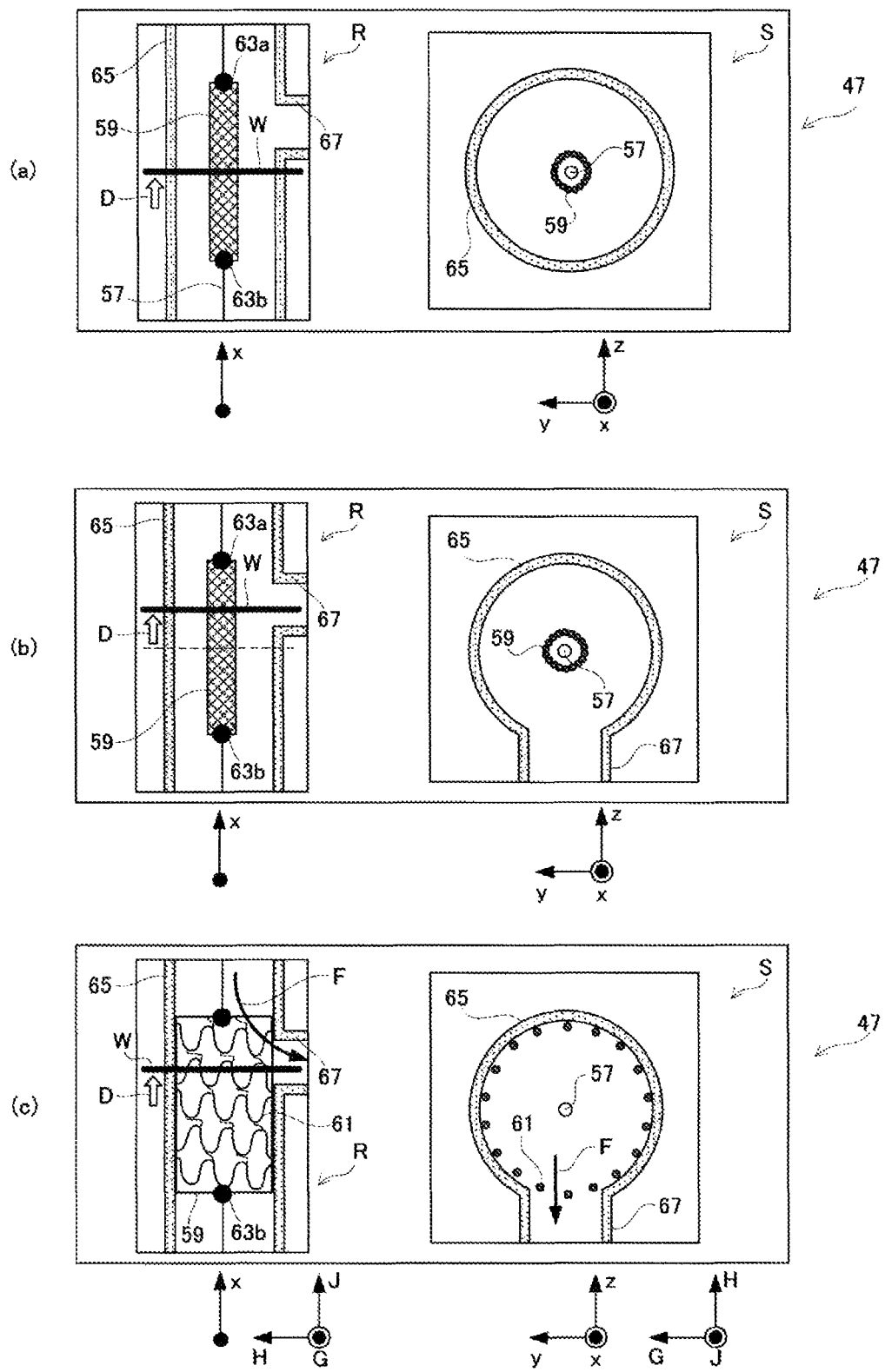
FIG. 10 is a diagram describing a step of Step S5 according to Example 1. (a) is a view illustrating a combined image displaying the segment image and the short-axis cross-sectional image in parallel, (b) is a view illustrating a combined image in a state in which the region-of-interest is translated in parallel, and (c) is a view illustrating a combined image in a state in which the stent is expanded.

As shown in FIG. 10 (*a*), the short-axis cross-sectional image S is displayed on the monitor 47 in parallel with the segment image R. The segment image R is an X-ray image (long-axis cross-sectional image) showing the long-axis direction cross-section for each of the stent 59 and the blood vessel 65, and the short-axis cross-sectional image S is an X-ray image showing the short-axis direction cross-section for each of the stent 59 and the blood vessel 65. In other words, the segment image R and the short-axis cross-sectional image S are X-ray images to be displayed on orthogonal planes, respectively. Therefore, by referring to the segment image R and the short-axis cross-sectional image S, a surgeon can confirm the three-dimensional information about the position of the stent 59 in the blood vessel 65.

When checking the three-dimensional information of the stent 59 at another position, as shown in FIG. 10 (*b*), a surgeon operates the input unit 45 to move the position of the region-of-interest W from the position indicated by the dotted line to the position indicated by the solid line. Then, when an instruction to reconstruct the three-dimensional image is input to the input unit 45, the reconstruction unit 41 generates a three-dimensional image for the region-of-interest W after the movement, and the cross-sectional image generation unit 43 generates a short-axis cross-sectional image S based on the viewpoint direction indicated by the arrow D. By referring to the short-axis cross-sectional image S, a surgeon can confirm the state in which the branched blood vessel 67 extends from the blood vessel 65 in the z-direction. A surgeon can also change the region-of-interest W and the viewpoint direction D by operating the input unit 45. In this case, the cross-sectional image generation unit 43 regenerates a short-axis cross-sectional image S based on the changed region-of-interest W and the viewpoint direction D.

Further, by referring to a combined image in which the segment image R and the short-axis cross-sectional image S are arranged in parallel, a surgeon can confirm more accurate information about the expanded state of the stent 59. In other words, when the stent 59 is expanded as shown in FIG. 10 (*c*), if only the segment image R which is a long-axis cross-sectional image is referred, it is difficult to confirm whether or not the stent 59 has sufficiently expanded in the depth direction (G-direction) of the stent 59. However, by referring to the short-axis cross-sectional image S, it is possible to accurately confirm whether or not the stent 59 is sufficiently expanded and in contact with the inner wall of the blood vessel 65 for each of the H-direction and the G-direction.

Further, by referring to the short-axis cross-sectional image S, the position of each strut 61 can be confirmed. Therefore, in the case of advancing a second stent (not shown) in the direction indicated by the arrow F and passing between the struts 61 to the branched blood vessel 67, the second stent can be assuredly passed between the struts 61 in the proper position. For this reason, a treatment of a branched blood vessel stenosed segment by an inverse T-stent method or the like can be performed more precisely. In this way, a surgeon proceeds the operative procedure of the IVR with reference to these two X-ray images to perform the stent indwelling at the appropriate position with respect to the stenosed blood vessel.

Effects by Configuration of Example 1

Thus, in Example 1, a predetermined region including a part of the stent among the entire region of the two-dimensional image P is set as a region-of-interest. Then, an image of a region corresponding to the region-of-interest is extracted from each of the two-dimensional images P generated in one scan, a three-dimensional image is sequentially reconstructed using each of the extracted images.

In a conventional radiographic imaging apparatus, the entire image is reconstructed for each of the two-dimensional images generated by one scan to generate a three-dimensional image. In this case, the amount of computation required to reconstruct the three-dimensional image becomes enormous and complicated, so the time required to generate the three-dimensional image becomes very long. As a result, when acquiring a three-dimensional image during an IVR, a surgeon was wasting a time by merely waiting a long time until the three-dimensional image was generated.

On the other hand, in the radiographic imaging apparatus according to Example 1, a three-dimensional image is generated using an image corresponding to the region-of-interest. In other words, of the two-dimensional images, only the region that needs to reconstruct the three-dimensional image is arbitrarily set as a region-of-interest and the region-of-interest is reconstructed. The range of the region-of-interest corresponds to a small part of the entire two-dimensional image. Therefore, in Example 1, it is possible to drastically shorten the time required to generate the three-dimensional image as compared with the conventional example. As a result, it is possible to quickly acquire the three-dimensional image including the required area, so that the time required for an IVR can be greatly shortened, which in turn can reduce the burden on the surgeon and the subject.

The reconstruction unit 41 sequentially performs reconstruction processing using the image of the region-of-interest which are sequentially transmitted. Therefore, a surgeon will not have to idly wait until the rotation imaging completes and all of the two-dimensional images are generated. That is, a surgeon can confirm the information of the three-dimensional image Tw which is gradually reconstructed during the execution of the rotation imaging with the monitor 47. Then, when the image of the region-of-interest related to the last two-dimensional image is transmitted, the reconstruction of the three-dimensional image has almost been completed, so that an accurate three-dimensional image Tw will be completed almost at the same time when the rotation imaging of the imaging system is completed. As a result, the time required to complete the three-dimensional image Tw can be further shortened.

Then, the cross-sectional image generation unit 43 generates a short-axis cross-sectional image based on the information of the three-dimensional image and the viewpoint direction. The short-axis cross-sectional image is displayed on the monitor in parallel with the segment image which is a long-axis cross-sectional image. A surgeon can confirm that the stent 59 is expanded not only in the vertical direction (H-direction) but also in the depth direction (G-direction) so that the strut 61 is in close contact with the entire inner wall of the blood vessel 65 by referring to the short-axis cross-sectional image.

The segment image is an X-ray image of a cross-section parallel to the x-direction, and an X-ray image of a cross-section orthogonal to the x-direction. The monitor 47 displays these two X-ray images in which the viewpoint directions are orthogonal to each other in parallel. For that reason, a surgeon can grasp the position and the expansion state of the stent 59 in the blood vessel 65 in detail for each of the x-direction, the y-direction, and the z-direction in the three-dimensional space by referring to two X-ray images to be displayed in parallel.

Therefore, the stent 59 can be more assuredly brought into close contact with the stenosed segment of the blood vessel 65 in an IVR, so it is possible to more assuredly avoid restenosis of the blood vessel 65 after the operative procedure. In addition, when treating a branch blood vessel by an inverse T-stent method, since it is possible to confirm the position between appropriate struts to be passed through the second stent with respect to the first stent, a surgeon can perform the stent indwelling appropriately with respect to the branch blood vessel. As described above, by performing an IVR using the radiographic imaging apparatus according to Example 1, it becomes possible to perform an endovascular treatment requiring three-dimensional image data quickly and more precisely.

Example 2

Next, Example 2 of the present invention will be described with reference to the attached drawings. As for the configuration common to Example 1, the same reference numerals are allotted, and the detailed description thereof will be omitted.

Figure 11:
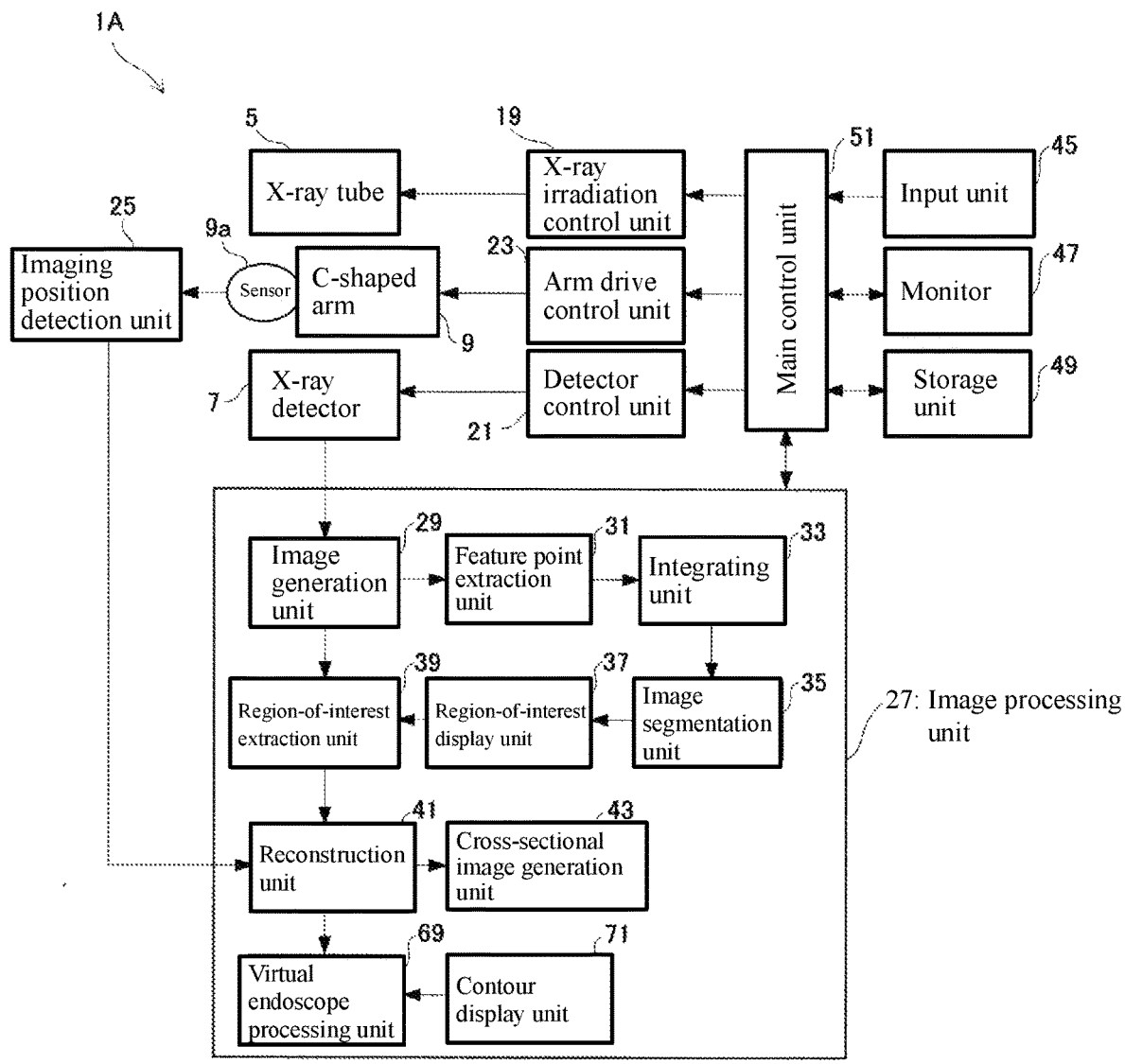
FIG. 11 is a functional block diagram illustrating a configuration of a radiographic imaging apparatus according to Example 2.

As shown in FIG. 11, the radiographic imaging apparatus 1A according to Example 2 is further provided with a virtual endoscope processing unit 69 and a contour display unit 71. The virtual endoscope processing unit 69 is provided at the subsequent stage of the reconstruction unit 41, and performs virtual endoscope processing on the three-dimensional image to generate a virtual endoscope image. The specific contents of the virtual endoscope processing will be described later. The virtual endoscope processing unit 69 corresponds to the virtual endoscope image generation means in the present invention.

The contour display unit 71 is connected to the virtual endoscope processing unit 69. The contour display unit 71 sequentially connects each strut of the stent reflected in the X-ray image to detect the outline of the stent, and displays the outline of the stent in the image. As a configuration for detecting the contour of the stent, a differential filter, such as, e.g., a Sobel filter, can be exemplified. The contour display unit 71 corresponds to the contour display means in the present invention.

Description of Operation Characteristic in Example 2

Next, the operation of the radiographic imaging apparatus 1A according to Example 2 will be described. FIG. 4 (*b*) is a flowchart related to the operation of Example 2. The steps from Step S1 to Step S5 are common to those in Example 1, and therefore the description thereof will be omitted and the step of Step S6 which is characteristic in Example 2 will be described. In Example 2, it is assumed that the range of the region-of-interest W is a rectangular area shown on the left side of FIG. 12 (*a*).

Figure 12:
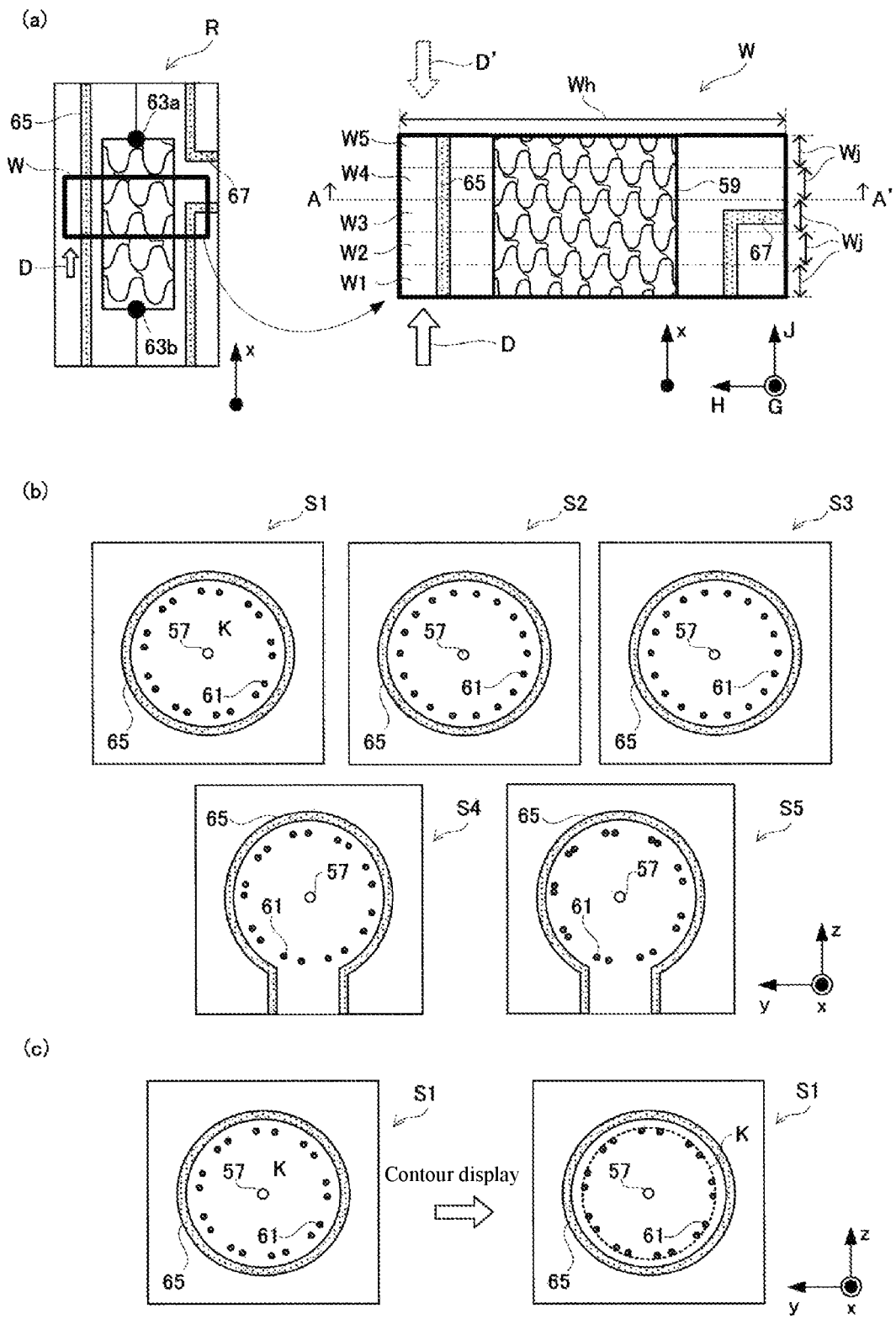
FIG. 12 is a diagram illustrating the operation of the radiographic imaging apparatus according to Example 2. The left figure (a) is a diagram illustrating the region-of-interest displayed in the segment image, and the right figure (b) is a diagram illustrating a small region configuring the region-of-interest in at state in which the region-of-interest is expanded. (b) is a diagram showing a short-axis cross-sectional image generated in each of the small regions, and (c) is a diagram showing a short-axis cross-sectional image in which the contour of the stent is illustrated.
Figure 13:
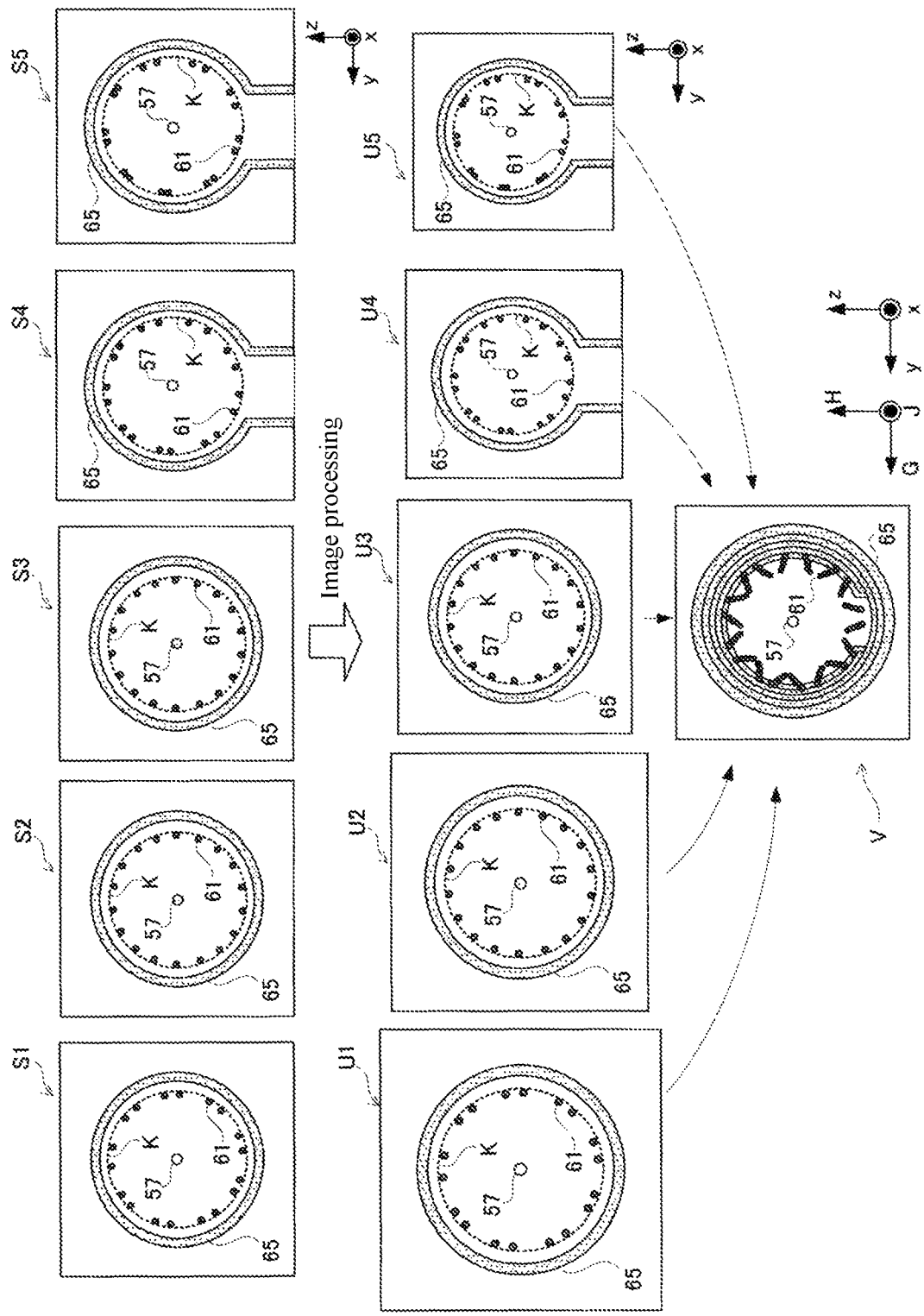
FIG. 13 is a diagram illustrating the step of Step S6 according to Example 1. The upper row illustrates each of short-axis cross-sectional images before performing image processing, the middle row illustrates each of short-axis cross-sectional images after performing the image processing, and the lower row illustrates a virtual endoscope image generated by superimposing short-axis cross-sectional images after performing the image processing.

The region-of-interest W can be divided into a plurality of small regions arranged along the long-axis of the stent 59 (FIG. 12 (*a*), right drawing). Although the number of small regions can be determined arbitrarily, the number of small regions is five in Example 2. With respect to each of the small regions, the description will be made by allotting the reference numerals W1 to W5 in the order from the side closer to the arrow D. That is, when the viewpoint direction is reversed and the arrow D is set as the arrow D', the order of the small areas W1 to W5 is reversed. In this case, the small region (small region W5 in FIG. 12 (*a*)) closest to the arrow D' is the small region W1.

Each of the small regions W1 to W5 is a rectangular region extending in the short-axis direction H of the stent 59, and the length in the H-direction coincides with the length Wh of the region-of-interest W in the H-direction. In the same manner as in Example 1, the length Wh is preferably about 4 mm for diagnosis. The lengths of the small regions W1 to W5 in the J-direction can be arbitrarily determined, but it is preferable that the lengths of the small regions W1 to W5 in the J-direction be all the same. Further, in order to generate a virtual endoscope image having a high degree of resolution, it is preferable that the length Wj of the small regions W1 to W5 in the J-direction be short. In other words, it is more preferable that the length Wj be a length corresponding to 1 pixel of the X-ray image.

Step S6 (Generation of Virtual Endoscope Image)

In Step S5, in the same manner as in Example 1, after generating a three-dimensional image Tw in the region-of-interest W, a virtual endoscope image is generated. The virtual endoscope processing unit 69 generates a short-axis cross-sectional image S when the three-dimensional image in each of the small regions W1 to W5 are viewed from the direction indicated by the arrow D, using the three-dimensional image Tw. Hereinafter, the short-axis cross-sectional image as viewed from the arrow D for the small regions Wn (n=1, . . ., 5) is denoted as a short-axis cross-sectional image Sn.

As an example, the short-axis cross-sectional image S4 is a short-axis cross-sectional image when the three-dimensional image obtained by reconstructing the small region W4 as a region-of-interest is viewed from the direction indicated by the arrow D. That is, when the viewpoint direction is the arrow D, the short-axis cross-sectional image S4 corresponds to the cross-sectional view taken along the line A-A' (see FIG. 12 (a)). In this way, the virtual endoscope processing unit 69 generates a plurality of short-axis cross-sectional images S1 to S5 as shown in FIG. 12 (b) according to the number of small regions.

The virtual endoscope processing unit 69 displays the blood vessel wall of the blood vessel 65 and the lumen of the blood vessel 65 (the inside of the blood vessel wall) so as to be distinguishable in each of the short-axis cross-sectional images Sn. As an example, in cases where the region of the blood vessel wall and the region of the inside of the blood vessel can be distinguishably detected based on the CT value (pixel value) in the short-axis cross-sectional image S, the virtual endoscope processing unit 69 displays the region of the blood vessel wall in the blood vessel 65 in an opaque manner based on the difference in the CT value (see the region shown by the halftone dot in the lower right drawing of FIG. 9). On the other hand, the region of the lumen of the blood vessel 65 is displayed transparent. However, in the lumen region of the blood vessel 65, the configuration that becomes the target of interest, such as, e.g., the catheter system 53, is displayed opaque based on the CT value. In Example 1, it is assumed that the blood vessel wall and the lumen can be distinctively displayed based on the CT value, and the process of generating the virtual endoscope image will be described below.

Here, the contour display unit 71 appropriately displays the contour of the stent 59 for each of the short-axis cross-sectional images S1 to S5 as necessary. That is, the strut 61 reflected in each of the short-axis cross-sectional images S is sequentially connected to detect the contour of the stent 59. The detection of the contour is performed using a differential filter, such as, e.g., a Sobel filter. The contour of the detected stent 59 is displayed as a circular line indicated by the reference symbol K in the short-axis cross-sectional image S (FIG. 12 (c), right drawing).

When the stent 59 is sufficiently expanded, the contour K becomes a large perfect circle. When the stent 59 is insufficiently expanded, the contour K becomes a small circular shape. And, when the stent 59 is not expanded evenly, the contour K becomes a distorted circular shape. By referring to the shape of the contour K, a surgeon can confirm whether or not the stent 59 has been equally and sufficiently expanded.

Figure 15:
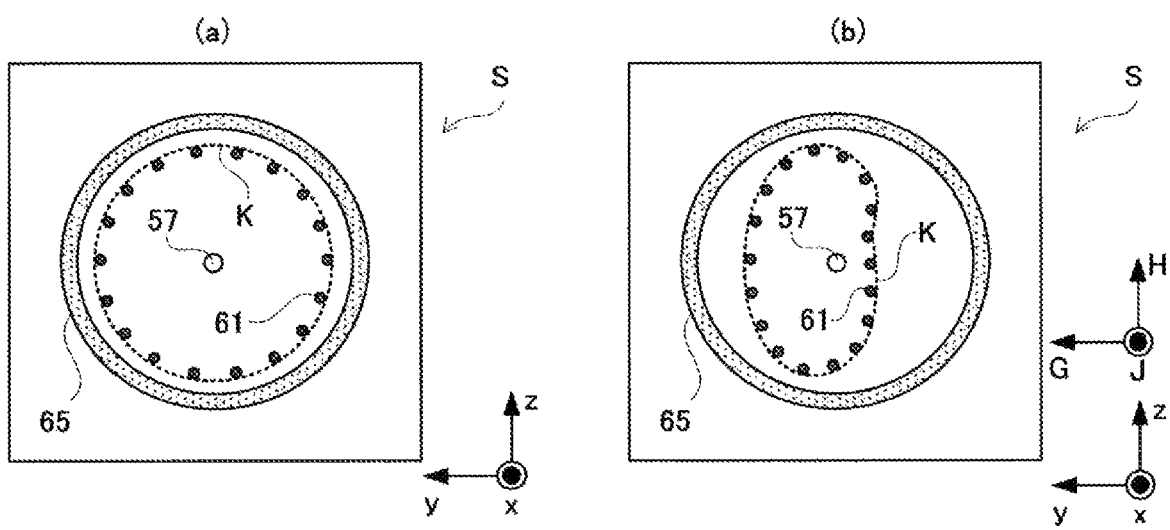
FIG. 15 is a diagram illustrating a short-axis cross-sectional image in which the contour of the stent is reflected in a radiographic imaging apparatus according to a modified example. (a) is a diagram showing the contour of the stent in the case in which the stent is uniformly expanded, and (b) is a diagram showing the contour of the stent in the case in which the stent is unevenly expanded.

The virtual endoscope processing unit 69 performs image processing for appropriately expanding or reducing each of the short-axis cross-sectional images S1 to S5 in which the contour K is reflected according to the distance from the viewpoint position. The virtual endoscope processing unit 69 performs image processing of each short-axis cross-sectional image S so that the short-axis cross-sectional image S which is closer to the arrow D becomes relatively large and the short-axis cross-sectional image S which is farther from the arrow D becomes relatively small. In Example 2, as shown in FIG. 15, the image processing is performed such that among the short-axis cross-sectional images S1 to S5, the short-axis cross-sectional image S1 becomes the largest and the short-axis cross-sectional image S5 becomes the smallest. Hereinafter, the short-axis cross-sectional images S1 to S5 on which the enlargement or reduction image processing is performed will be referred to as processed cross-sectional images U1 to U5.

The virtual endoscope processing unit 69 superimposes the processed cross-sectional images U1 to U5 to generate a virtual endoscope image V. In the virtual endoscope image V, the image of the contour K of the stent 59 is omitted. In the virtual endoscope image V, as the distance to the viewpoint direction indicated by arrow D increases, the X-ray image is displayed so as to be small in the center of the image. By displaying each short-axis cross-sectional image in a tunnel shape, the virtual endoscope image V is displayed as if the lumen of the blood vessel 65 and the stent 59 were reflected as if an endoscopic observation is performed.

Figure 14:
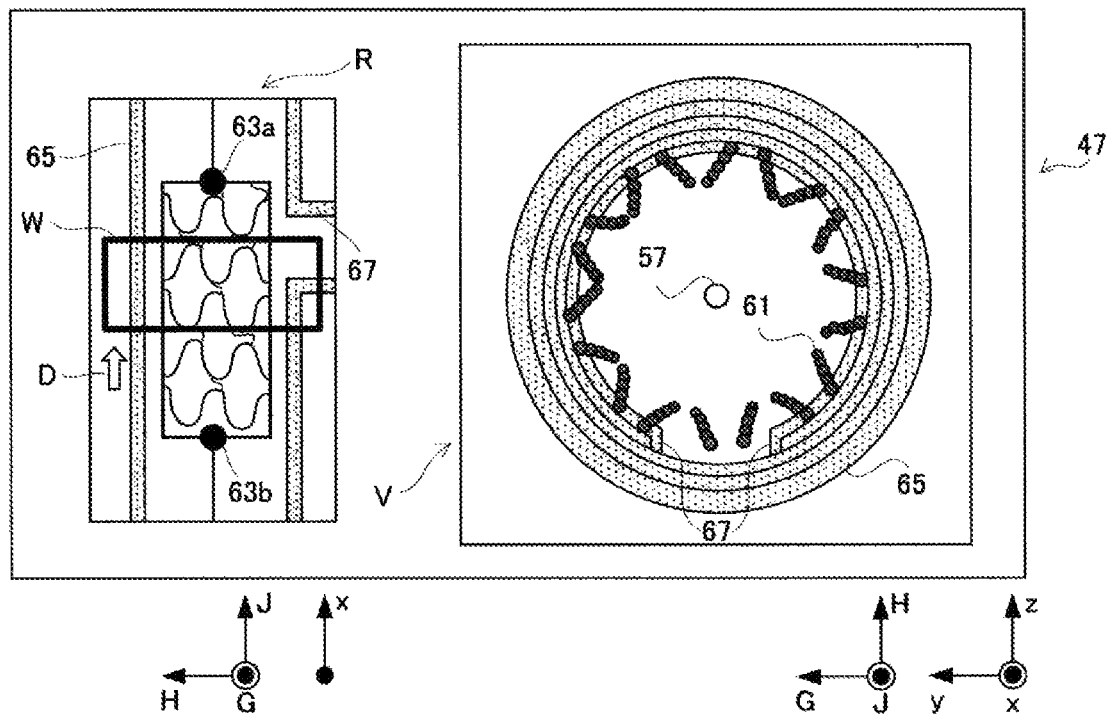
FIG. 14 is a diagram illustrating a combined image according to Example 2.

For example, the image of the branched blood vessel 67 reflected in the processed cross-sectional images U4 and U5 is reflected relatively close to the center of the image as a relatively small image in the virtual endoscope image V (FIG. 14). Therefore, a surgeon can confirm that the intersection of the blood vessel 65 and the branched blood vessel 67 is located at the back in the x-direction and the branched blood vessel 67 extends downward from the intersection in the z-direction by referring to the virtual endoscope image V.

As shown in FIG. 14, the virtual endoscope image V is displayed on the monitor 47 in parallel with the segment image R. A surgeon refers to the combined image in which the segment image R and the virtual endoscope image V are arranged in parallel and proceeds with the operative procedure of the IVR. A surgeon can confirm two-dimensional information about a plane parallel to x-direction with reference to the segment image R by referring to the segment image R and can confirm pseudo three-dimensional information about a plane orthogonal to the x-direction by referring to the virtual endoscope image V.

Also, a surgeon can change the position and the size of the region-of-interest W as necessary by manipulating the input unit 45. Then, by inputting an instruction to reconstruct a three-dimensional image to the input unit 45, the reconstruction unit 41 generates a three-dimensional image of the region-of-interest W after the movement, and the virtual endoscope processing unit 69 generates the virtual endoscope image V based on the viewpoint direction indicated by the arrow D.

When the position of the region-of-interest W is moved in the x-direction, the X-ray image reflected in the virtual endoscope image V changes as if it moved forward and backward in the blood vessel. When the range of the region-of-interest W is expanded to be longer in the x-direction, the virtual endoscope image V becomes a more depth image in the x-direction. A surgeon proceeds with the operative procedure of the IVR while referring to the combined image and performs stent indwelling at an appropriate position for the stenosed blood vessel.

The contour display unit 71 can also display so that the outside and the inside of the contour of the stent 59 denoted by the reference symbol K can be distinguishable. In the short-axis cross-sectional image S, it is often difficult to distinguish between the actual blood vessel wall and the inside of the blood vessel wall due to the difference in the CT value. Therefore, by displaying the contour of the stent 59 as a boundary line so as to distinguish between the outside and the inside, the virtual endoscope image V can be suitably generated even in cases where it is difficult to distinguish between the blood vessel wall and the inside of the blood vessel wall based on the CT value.

That is, in cases where it is difficult to distinguish between the blood vessel wall and its inside based on the CT value, a surgeon operates the input unit 45 to change from a mode in which the blood vessel wall is extracted based on the CT value as a reference and is distinguishably displayed to a mode in which the blood vessel wall is distinguishably displayed based on the contour K of the stent 59. In accordance with the mode change, for each short-axis cross-sectional image S, the contour display unit 71 opaquely displays the outside of the contour K of the stent 59 as a region corresponding to the blood vessel wall and transparently displays the inside of the contour K as a region corresponding to the blood vessel lumen.

Then, by superimposing the processed cross-sectional images U1 to U5 distinctively displayed with the contour K as a boundary, the virtual endoscope processing unit 69 generates a virtual endoscope image V. Generally, in the blood vessel lumen, the stent 59 is expanded so as to inscribe the blood vessel wall of the blood vessel 65. Therefore, by detecting the contour of the stent 59 and further distinctively displaying the inside and the outside with the contour K of the stent 59 as a boundary line, the virtual endoscope image V capable of suitably distinguishing the blood vessel wall and the blood vessel lumen of the blood vessel 65 can be more assuredly generated.

Effects by Configuration of Example 2

In the configuration according to Example 1, the cross-sectional image generation unit 43 generates a single short-axis cross-sectional image S based on the reconstructed three-dimensional image Tw on the region-of-interest W. Here, the image generated by the cross-sectional image generation unit 43 corresponds to a short-axis cross-sectional image when the three-dimensional image Tw is viewed from the direction indicated by the arrow D, that is, the short-axis cross-sectional image S1. Then, a short-axis cross-sectional image S1 displaying the two-dimensional information of the short-axis direction is displayed in parallel with the segment image R.

On the other hand, in Example 2, the virtual endoscope processing unit 69 generates a short-axis cross-sectional image of each small region viewed from the direction indicated by the arrow D based on the reconstructed three-dimensional image Tw on the region-of-interest W, i.e., a plurality of short-axis cross-sectional images S1 to S5. Then, the short-axis cross-sectional images S1 to S5 are each image-processed with different magnification ratios and superimposed to generate a virtual endoscope image V. The virtual endoscope image V displaying the pseudo three-dimensional information in the short-axis direction is displayed in parallel with the segment image R.

By referring to the virtual endoscope image V, a surgeon can also confirm the information on the depth in the long-axis direction (J-direction) for the lumen of the blood vessel 65 and the stent 59. Therefore, by conducting an IVR using the radiographic imaging apparatus 1A according to Example 2, it is possible to acquire more accurate information on the three-dimensional position and the extension state of the stent 59 inside the blood vessel 65.

In the same manner as in Example 1, the three-dimensional image Tw used to generate the virtual endoscope image V is reconstructed based on the image corresponding to the region-of-interest W extracted from each of the two-dimensional images P. Since the range of the region-of-interest is only a small part of the entire two-dimensional image, the time required to generate a three-dimensional image can be greatly shortened. As a result, since the virtual endoscope image can be acquired quickly, the time required for an IVR can be greatly shortened, which in turn can reduce the burden on the surgeon and the subject.

The contour display unit 71 sequentially connects the images of the strut 61 and detects the contour K of the stent 59. Since the contour K is detected using a differential filter, such as, e.g., a Sobel filter, the contour K to be displayed is an image which accurately reflects the position of the outline of the stent 59. With such a configuration, even in cases where the stent 59 is expanded so that the spacing between the struts 61 is widened, the position of the contour of the stent 59 can be accurately confirmed. Therefore, a surgeon can more precisely confirm the three-dimensional position information of the stent 59 in the lumen of the blood vessel 65 by referring to the virtual endoscope image V.

The present invention is not limited to the aforementioned Examples, and can be modified as follows.

(1) In each of Examples described above, the contour display unit 71 may configured to be connected to the cross-sectional image generation unit 43 as well. In this case, the contour display unit 71 connects the position of the strut 61 of the stent 59 with a line in the short-axis cross-sectional image S and displays the contour K of the stent 59. When the stent 59 is sufficiently expanded, as shown in FIG. 15 (*a*), the contour K has a large perfect circle shape. When the stent 59 is insufficiently expanded, the contour V becomes a small circular shape.

When the stent 59 is not expanded evenly, as shown in FIG. 15 (*b*), the contour V has a distorted circular shape. With such a configuration, even in cases where the stent 59 is expanded so that the spacing between the struts 61 is widened in Example 1, the position of the contour of the stent 59 can be accurately confirmed in a combined image.

By referring to the shape of the contour K, a surgeon can more accurately confirm whether or not the stent 59 is uniformly and sufficiently expanded and brought into close contact with the inner wall of the blood vessel 65. Therefore, the stent 59 can be more assuredly brought into close contact with the stenosed segment of the blood vessel 65 in an IVR, so it is possible to more assuredly avoid restenosis of the blood vessel 65 after the operative procedure.

(2) In each of the above-described Examples, in Step S3, the extraction of the marker 63, the generation of the integrated image Q, and the generation of the segment image R are performed, but the steps of extracting the marker 63 and generating the integrated image Q may be omitted. In this case, the segment image R is generated using one of two-dimensional images P. It is more preferable that the image used be a two-dimensional image Pe which is a two-dimensional image P generated most recently. That is, the image segmentation unit 35 segments the images of the stent 59 and the neighboring regions of the stent 59 from the two-dimensional image Pe and appropriately rotates and enlarges the image to generate the segment image R. In such a modified example, since the configuration of the feature point extraction unit 31 and the integrating unit 33 can be omitted, the configuration of the radiographic imaging apparatus can be further simplified.

Figure 16:
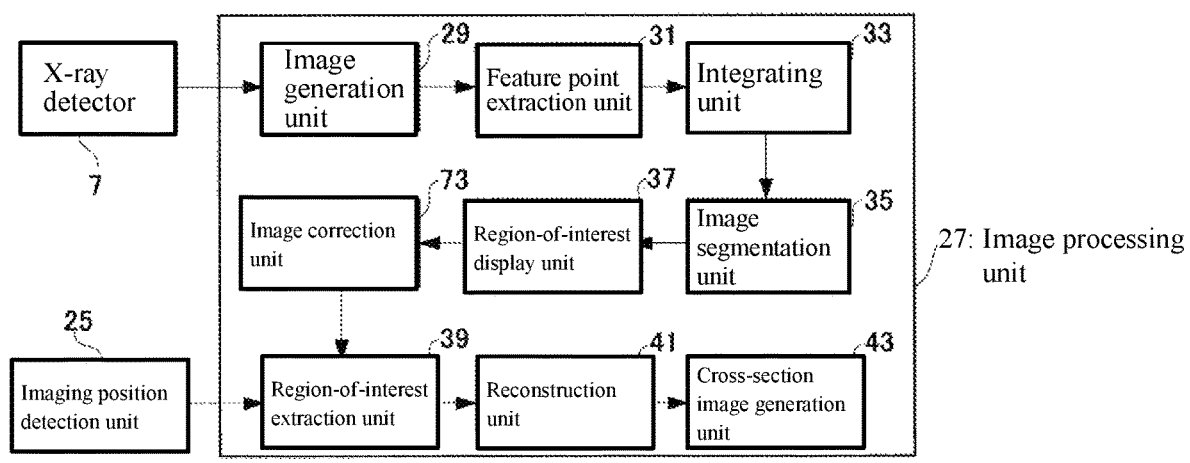
FIG. 16 is a functional block diagram illustrating a configuration of an image processing unit in a radiographic imaging apparatus according to a modified Example.
Figure 17:
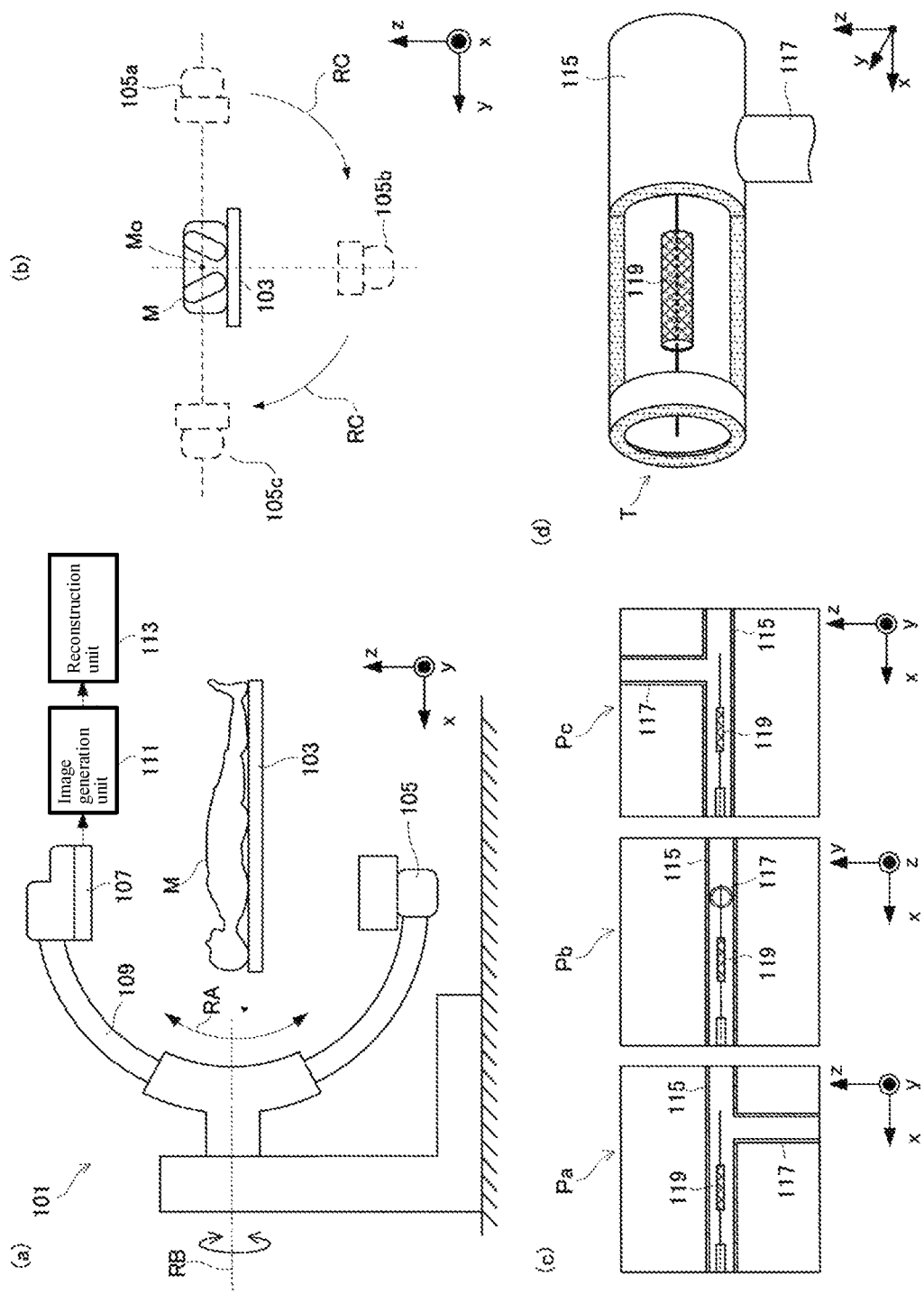
FIG. 17 is a diagram illustrating a configuration of a radiographic imaging apparatus according to a conventional example. (a) is a front view illustrating a configuration of a radiographic imaging apparatus according to a conventional example, (b) is a diagram illustrating each imaging position in one scan, (c) is a diagram illustrating a two-dimensional image generated in each imaging position, and (d) is a diagram illustrating a three-dimensional image according to a conventional example, which is generated by reconstructing each of the entire two-dimensional images.

(3) In the above-described Examples, when generating the three-dimensional image Tw, an image corresponding to the region-of-interest W is extracted without performing image processing on each of the two-dimensional images Pa to Pe, but the present invention is not limited to such a configuration. That is, as shown in FIG. 16, in the image processing unit 27, an image correction unit 73 may be provided at a subsequent stage of the region-of-interest display unit 37 and at a preceding stage of the region-of-interest extraction unit 39. To the image correction unit 73, each of the two-dimensional images P in which the feature point extraction unit 31 extracts the marker 63 is transmitted.

In the configuration according to such a modification (3), the image correction unit 73 performs a position adjustment of the stent 59 on the basis of the marker 63 for each of the two-dimensional images Pa to Pe by image conversion processing, such as, e.g., an affine transformation. Then, the region-of-interest extraction unit 39 extracts an image corresponding to the region-of-interest W from each of the two-dimensional images Pa to Pe after image conversion processing. The reconstruction unit 41 reconstructs each of the extracted images to generate a three-dimensional image Tw.

In the case of such a modification, even in cases where the stent moves at high speed at any time due to a heartbeat, etc., such as a heart vessel intervention (PCI), by reconstructing based on the two-dimensional image data after the image conversion processing, high quality three-dimensional image data can be acquired in real time. Therefore, it is possible to quickly acquire a high-quality three-dimensional image that reflects the stent in the cardiac blood vessel during the operative procedure of the PCI, which was considered impossible to realize so far.

(4) In each of Examples described above, the description is made using the stent as the device, but the device which is an object of capturing the three-dimensional image is not limited to a stent. Another example of the device is a roller bladder used for an atherectomy. In this case, by referring to the segment image and the short-axis cross-sectional image (or the virtual endoscope image) with a single monitor 47, the position of the roller bladder can be appropriately controlled. Therefore, a surgeon can more assuredly cut an atheroma and/or a calcified blood vessel wall. Therefore, it is possible to assuredly avoid cutting the normal blood vessel wall by mistake by the roller bladder, so it is possible to reduce the burden on the subject.

(5) In each of the above-described Examples, the description was directed to the case in which the body axis direction of the subject M and the long-axis direction of the stent 59 are parallel and the C-shaped arm 9 rotates about the axis of the body axis direction (x-direction) of the subject M, but the direction of the rotation axis of the C-shaped arm 9 is not limited to the axial direction parallel to the x-direction. That is, the direction of the rotation axis of the C-shaped arm 9 may be appropriately changed according to the long-axis direction of the stent 59.

As an example, in cases where the long-axis direction J of the stent 59 is different from the body axis direction of the subject M, a surgeon operates the input unit 45 to change the direction of the rotation axis of the C-shaped arm 9 when generating the two-dimensional image P in Step S2. The rotation axis direction of the C-shaped arm 9 is adjusted so as to be substantially parallel to the long-axis direction J of the stent 59. In this case, the imaging system composed of the X-ray tube 5 and the X-ray detector 7 moves along the arc orbit which rotates about the axis in a predetermined direction which is substantially parallel to the J-direction. As a result, in each of the two-dimensional image P, the X-ray image of the stent 59 in the long-axis direction is suitably displayed. In this case, the short-axis cross-sectional image S is generated for a plane orthogonal to the rotation axis direction of the C-shaped arm 9 after the change.

(6) In each of the aforementioned Examples, the description was directed to the case in which the body axis direction of the subject M and the long-axis direction of the stent 59 are parallel and the short-axis cross-sectional image S is generated for the yz-plane orthogonal to the body axis direction of the subject M as an example, the cross-section where the short-axis cross-sectional image S is generated is not limited to a plane orthogonal to the x-direction. That is, according to the long-axis direction of the stent 59, the direction of the plane on which the short-axis cross-sectional image S is generated may be appropriately changed. In this case, the short-axis cross-sectional image S is generated for a plane different from the plane on which the segment image R is generated.

In the configuration according to the modified Example (6), the image processing unit 27 can calculate the J-direction which is the long-axis direction of the stent based on the information of the stent 59 and the marker 63 reflected on each of the two-dimensional images P. Based on the calculated long-axis direction information of the stent 63, the cross-sectional image generation unit 43 generates a short-axis cross-sectional image for a plane orthogonal to the J-direction.

(7) In each of Examples described above, after setting the region-of-interest W in Step S4, the three-dimensional image Tw is reconstructed in Step S5, but the timing of setting the region-of-interest W is changed may be changed. In other words, as an example, the order of Steps S4 and S5 may be switched, and the region-of-interest W may be arbitrarily set after reconstructing the three-dimensional image Tw. When a surgeon does not set the region-of-interest W when reconstructing the three-dimensional image Tw, the reconstruction unit 41 reconstructs the three-dimensional image Tw for the region-of-interest in the default state (for example, the predetermined region in the middle of the markers 63a and 63b). After changing the region-of-interest W, a three-dimensional image Tw and a short-axis cross-sectional image S are generated for the changed region-of-interest W.

(8) In Example 2 described above, the description is directed to the case in which the blood vessel wall of the blood vessel 65 or the contour K of the stent 59 are automatically detected as the boundary line and the outside and the inside of the boundary line in the virtual endoscope are automatically distinctively displayed in the virtual endoscope image, but it is not limited to the configuration that automatically detects the boundary line which is the reference of the section display. That is, in the virtual endoscope image, it may be configured such that the boundary line can be manually set.

In Example 2, the description is directed to the case in which it is possible to automatically detect the blood vessel wall of the blood vessel 65 and the contour of stent 59 as a boundary line based on the CT value. However, in the actual medical site, there is a case in which it is difficult to clearly extract the blood vessel wall of the blood vessel 65 and the contour of the stent 59 as a boundary line based on the difference in the CT value. In cases where it is difficult to automatically extract a distinct boundary line in the configuration according to the modified Example (8), a surgeon refers to the virtual endoscope image, etc., displayed on the monitor 47 and sets a substantially circular boundary line having a predetermined diameter by a manual operation using the input unit 45 or the like.

The virtual endoscope processing unit 69 displays the virtual endoscope image V so that it can be distinguished from the inside and outside of the boundary line set by a manual operation. As an example, the outside of the boundary line is displayed opaque as a region corresponding to the blood vessel wall, and the inside of the boundary line is transparently displayed as a region corresponding to the blood vessel lumen. By making it possible to manually set the boundary line for distinctively displaying the virtual endoscope image as described above, regardless of the quality of the three-dimensional image Tw, a high quality virtual endoscope image that can clearly be visually recognized a region corresponding to the blood vessel wall and a region corresponding to the blood vessel lumen.

(9) In the above-described Example 2, a contrast agent may be used to distinctly display the blood vessel wall and the blood vessel lumen more readily and clearly. That is, in the virtual endoscope image V, in cases where it is difficult to distinguish between the blood vessel wall and the blood vessel lumen of the blood vessel 65 based on difference of the CT value, the contrast agent is injected into the blood vessel 65 via the catheter 55. In the non-contrast state, the difference of the CT value between the blood vessel wall and the blood vessel lumen of the blood vessel 65 is small. However, in the contrast state, the contrast agent fills the blood vessel lumen, so the difference of the CT value between the blood vessel wall and the blood vessel lumen of the blood vessel 65 becomes large. As a result, it is very easy to distinctly display the blood vessel wall and the blood vessel lumen based on the CT value by the injection of the contrast agent.

DESCRIPTION OF REFERENCE SYMBOLS

1: radiographic imaging apparatus
3: top board
5: X-ray tube (radiation source)
7: X-ray detector (radiation detection means)
19: X-ray irradiation control unit (radiation irradiation control means)
23: arm drive control unit (imaging system moving means)
25: imaging position detection unit
29: image generation unit (image generation means)
31: feature point extraction unit (feature point extraction means, reference point extraction means)
33: integrating unit (integrating means)
35: image segmentation unit (image segmentation means)
37: region-of-interest display unit (region-of-interest display means)
39: region-of-interest extraction unit (region-of-interest extraction means)
41: reconstruction unit (reconstruction means)
43: cross-sectional image generation unit (short-axis cross-sectional image generation unit)
59: stent (device)
63: marker (feature point, reference point)
69: virtual endoscope processing unit (virtual endoscope image generation means)
71: contour display unit (contour display means)
73: image correction unit (image correction means)

The invention claimed is:

1. A radiographic imaging apparatus comprising:
a radiation source configured to irradiate radiation to a subject;
radiation detection means configured to detect the radiation transmitted through the subject;
imaging system moving means configured to move an imaging system composed of the radiation source and the radiation detection means along a predetermined orbit with respect to the subject;
radiation irradiation control means configured to control to make the radiation source repeat radiation irradiation while the imaging system moves along the predetermined orbit with respect to the subject;
image generation means configured to generate a two-dimensional image of a region including a device to be inserted into a body of the subject based on a radiation detection signal output by the radiation detection means each time the radiation source performs the radiation irradiation so as to generate a plurality of two-dimensional images;
feature point extraction means configured to extract a feature point from the plurality of two-dimensional images;
integrating means configured to generate an integrated image by superimposing the plurality of the two-dimensional images with the feature point extracted by the feature point extraction means as a reference;
region-of-interest receiving means configured to receive an input of setting of a region-of-interest including at least a part of the device on the integrated image; and
reconstruction means configured to reconstruct a three-dimensional image of the region-of-interest based on each of images corresponding to the region-of-interest in plurality of the two-dimensional images generated by the image generation means.

2. The radiographic imaging apparatus as recited in claim 1, further comprising:
image segmentation means configured to segment a portion of the device from the two-dimensional image to generate a segment image;
short-axis cross-sectional image generation means configured to generate a radiation image of a cross-section of the device orthogonal to a long-axis direction as a short-axis cross-sectional image based on the three-dimensional image; and
image display means configured to display the segment image and the short-axis cross-sectional image in parallel.

3. The radiographic imaging apparatus as recited in claim 2,
wherein the image segmentation means segments the portion of the device from the integrated image to generate the segment image.

4. The radiographic imaging apparatus as recited in claim 2, further comprising:
region-of-interest display means configured to display a range of the region-of-interest with respect to the segment image to be displayed on the image display means.

5. The radiographic imaging apparatus as recited in claim 4, further comprising:

region-of-interest setting means configured to arbitrarily set a position and a size of the region-of-interest to be reflected in the segment image, wherein the reconstruction means reconstructs a three-dimensional image of the region-of-interest based on each of images corresponding to the region-of-interest set by the region-of-interest setting means in the plurality of the two-dimensional images generated by the image generation means.

6. The radiographic imaging apparatus as recited in claim 2, further comprising:

virtual endoscope image generation means configured to generate a virtual endoscope image of the region-of-interest by correcting a size of each of the short-axis cross-sectional images to be generated based on the three-dimensional image so that the size becomes larger as it approaches a viewpoint for the short-axis cross-sectional image and superimposing corrected short-axis cross-sectional images.

7. The radiographic imaging apparatus as recited in claim 6, wherein the image display means displays the segment image and the virtual endoscope image in parallel.

8. The radiographic imaging apparatus as recited in claim 2, further comprising:

contour display means configured to display a contour of the device reflected in the short-axis cross-sectional image.

9. The radiographic imaging apparatus as recited in claim 1, further comprising:

reference point extraction means configured to extract a reference point from the two dimensional image; and image correction means configured to correct each of a series of the two-dimensional images based on the reference point so that a position of the device reflected in the two-dimensional image is the same, wherein the reconstruction means reconstructs three-dimensional image of the region-of-interst based on each of images corresponding to the region-of-interest in the plurality of the two-dimensional images corrected by the image correction means.

10. A radiographic imaging apparatus comprising:

a radiation source configured to irradiate radiation to a subject;

radiation detection means configured to detect the radiation transmitted through the subject;

imaging system moving means configured to move an imaging system composed of the radiation source and the radiation detection means along a predetermined orbit with respect to the subject;

radiation irradiation control means configured to control to make the radiation source repeat radiation irradiation while the imaging system moves along the predetermined orbit with respect to the subject;

image generation means configured to generate a two-dimensional image of a region including a device to be inserted into a body of the subject based on a radiation detection signal output by the radiation detection means each time the radiation source performs the radiation irradiation;

region-of-interest extraction means configured to extract a predetermined region including a part of the device as a region-of-interest from each of the two-dimensional images generated by the image generation means;

reconstruction means configured to reconstruct a three-dimensional image of the region-of-interest based on each of images corresponding to the region-of-interest extracted by the region-of-interest extraction means from each of a series of the two-dimensional images generated by the image generation means;

image segmentation means configured to segment a portion of the device from the two-dimensional image to generate a segment image;

short-axis cross-sectional image generation means configured to generate a radiation image of a cross-section of the device orthogonal to a long-axis direction as a short-axis cross-sectional image based on the three-dimensional image; and image display means configured to display the segment image and the short-axis cross-sectional image in parallel.

11. The radiographic imaging apparatus as recited in claim 10, further comprising:

feature point extraction means configured to extract a feature point from the two-dimensional image; and integrating means configured to generate an integrated image by superimposing a plurality of the two-dimensional images with the feature point extracted by the feature point extraction means as a reference, wherein the image segmentation means segments the portion of the device from the integrated image to generate the segment image.

12. The radiographic imaging apparatus as recited in claim 10, further comprising:

region-of-interest display means configured to display a range of the region-of-interest with respect to the segment image to be displayed on the image display means.

13. The radiographic imaging apparatus as recited in claim 12, further comprising:

region-of-interest setting means configured to arbitrarily set a position and a size of the region-of-interest to be reflected in the segment image, wherein the region-of-interest extraction means extracts an image corresponding to the region-of-interest from each of the two-dimensional images based on the region-of-interest set by the region-of-interest setting means.

14. The radiographic imaging apparatus as recited in claim 10, further comprising:

virtual endoscope image generation means configured to generate a virtual endoscope image of the region-of-interest by correcting a size of each of the short-axis cross-sectional images to be generated based on the three-dimensional image so that the size becomes larger as it approaches a viewpoint for the short-axis cross-sectional image and superimposing corrected short-axis cross-sectional images.

15. The radiographic imaging apparatus as recited in claim 14, wherein the image display means displays the segment image and the virtual endoscope image in parallel.

16. The radiographic imaging apparatus as recited in claim 10, further comprising:

contour display means configured to display a contour of the device reflected in the short-axis cross-sectional image.

17. The radiographic imaging apparatus as recited in claim 10, further comprising:

reference point extraction means configured to extract a reference point from the two dimensional image; and image correction means configured to correct each of a series of the two-dimensional images based on the reference point so that a position of the device reflected in the two-dimensional image is the same,
wherein the region-of-interest extraction means extracts an image of a portion corresponding to the region-of-interest from the series of the two-dimensional images corrected by the image correction means.

* * * * *